(12) United States Patent
Salhia

(10) Patent No.: US 10,525,148 B2
(45) Date of Patent: Jan. 7, 2020

(54) SYSTEMS AND METHODS FOR PRECLINICAL MODELS OF METASTASES

(71) Applicant: The Translational Genomics Research Institute, Phoenix, AZ (US)

(72) Inventor: Bodour Salhia, Phoeniz, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 207 days.

(21) Appl. No.: 14/668,260

(22) Filed: Mar. 25, 2015

(65) Prior Publication Data

US 2016/0051702 A1    Feb. 25, 2016

Related U.S. Application Data

(60) Provisional application No. 61/970,185, filed on Mar. 25, 2014.

(51) Int. Cl.
*A61K 49/00* (2006.01)
*C12Q 1/6809* (2018.01)

(52) U.S. Cl.
CPC ........ *A61K 49/0008* (2013.01); *C12Q 1/6809* (2013.01)

(58) Field of Classification Search
CPC ........ A61K 49/0008; A61K 2039/6025; A61K 31/397; A61K 31/4025; A61K 31/416; A61K 31/4245; A61K 31/428; A61K 31/437; A61K 31/5375; A61K 39/0011; C12Q 1/6809; C12Q 2535/122; C12Q 2539/105; C12Q 1/6886; C12Q 2600/156; C12Q 2600/158; C12Q 2600/106; C12Q 2600/16; C12Q 1/6869; C12Q 2537/165; C12Q 1/6804; C12Q 2600/112; C12Q 2600/118; C12Q 2600/154; C12Q 2600/178; C12N 15/111; C12N 15/115; C12N 2310/14; C12N 2310/141; C12N 2310/16; C12N 2310/3513; C12N 2310/531; C12N 2320/10; G01N 33/5076; G01N 33/53; G01N 33/57484; G01N 33/57488; G16H 50/20; Y02A 90/26
USPC ......... 506/2; 800/10, 3; 435/6.12, 375, 6.11, 435/188, 252.33, 254.2, 287.2, 320.1, 435/325, 348, 358, 364, 365, 7.2, 7.21, 435/501
See application file for complete search history.

(56) References Cited

U.S. PATENT DOCUMENTS

2013/0244885 A1* 9/2013 Wang .................. C12Q 1/6804
506/2

OTHER PUBLICATIONS

DeRose et al. vol. 17 | No. 11 | Nov. 2011 Nature Medicine, 1514-1520.*
Salhia et al. PLOS One, Jan. 2014 | vol. 9 | Issue 1 | e85448, pp. 1-13.*

* cited by examiner

*Primary Examiner* — Janet L Epps-Smith
(74) *Attorney, Agent, or Firm* — Rodney J. Fuller; Booth Udall Fuller, PLC

(57) ABSTRACT

Embodiments of the invention provide methods of creating clinical models for different forms of metastatic cancer. The methods may include obtaining samples from subjects with metastatic cancer, determining an allelic status of one or more markers in the samples (e.g., creating a molecular profile of the subject's cancer), and using model organisms with subject-derived xenografts for treatment selection.

20 Claims, 23 Drawing Sheets
(23 of 23 Drawing Sheet(s) Filed in Color)

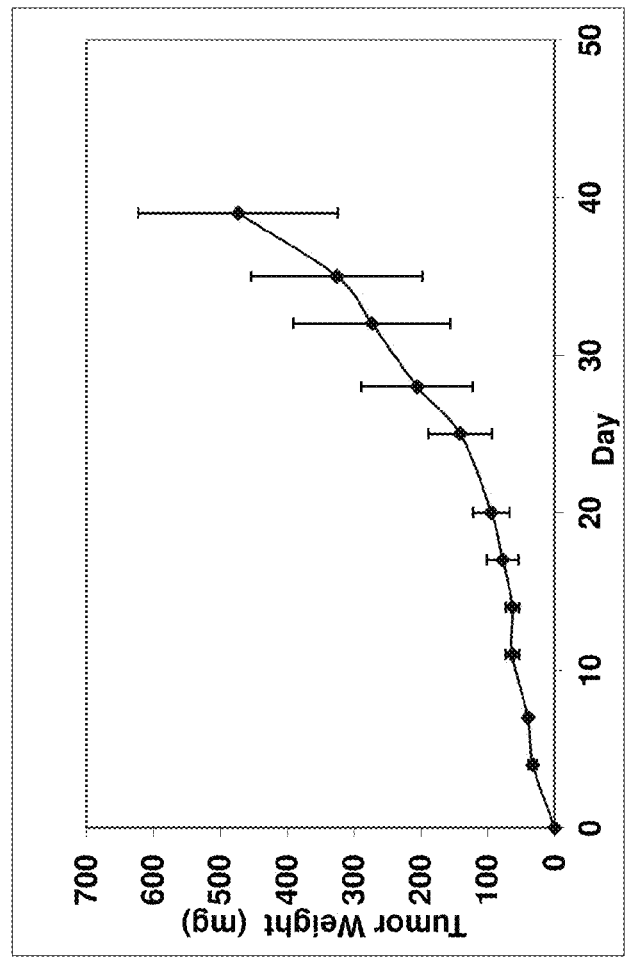
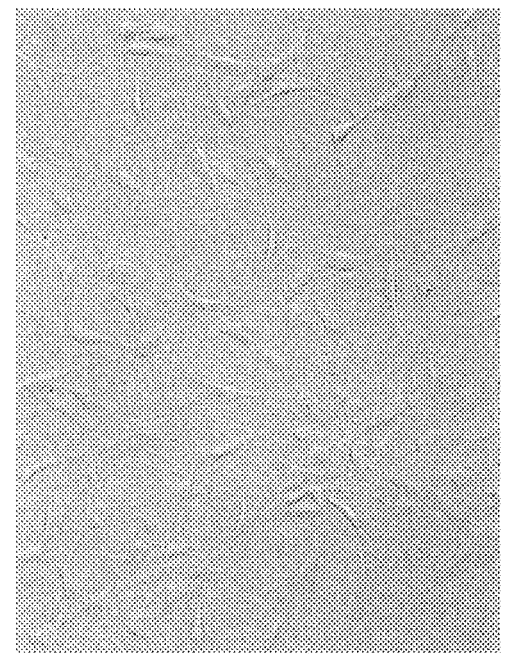
FIG. 2A
FIG. 2B

| Origin | Sample ID | Original Sample | PDX | Cell Line | Primary Tissue | Blood |
|---|---|---|---|---|---|---|
| NSCL | 1 | ✓ | ✓ | | ✗ | ✓ |
| NSCL-spine | 2 | ✓ | ✓ | | ✓ | ✓ |
| NSCL | 3 | ✓ | ✗ | | ✗ | ✓ |
| NSCL | 4 | ✗ | ✗ | | ✗ | ✓ |
| NSCL | 5 | ✓ | ✗ | | ✓ | ✓ |
| NSCL | 6 | ✓ | ✗ | | ✗ | ✓ |
| NSCL | 7 | ✓ | ✓ | | ✓ | ✓ |
| SCLC | 8 | ✓ | ✓ | | | ✓ |
| SCLC | 9 | ✓ | ✓ | ✓ | | ✓ |
| NSCL | 10 | ✓ | ✓ | | | ✓ |
| Breast | 11 | ✓ | ✓ | ✓ | ✓ | ✓ |
| Breast | 12 | ✓ | ✓ | | | ✓ |
| Breast | 13 | ✓ | ✓ | | | ✓ |
| Colon | 14 | ✓ | ✓ | | | ✓ |
| | | 14 | 10 | | | |

FIG. 9

SYSTEMS AND METHODS FOR PRECLINICAL MODELS OF METASTASES

CROSS-REFERENCE TO RELATED APPLICATIONS

This application claims the priority of U.S. provisional application No. 61/970,185 filed Mar. 25, 2014, the contents of each of which are hereby incorporated by reference in their entirety for all purposes

FIELD OF THE INVENTION

The present invention is generally related to systems and methods of cancer characterization, and particularly related to systems and methods for the creation of preclinical models of metastases and potential therapeutic selections based on the characterizations.

BACKGROUND OF THE INVENTION

Central nervous system (CNS) metastasis is the most common intracranial tumor, and has a yearly incidence of over 170,000 new cases in the United States (Al-Shamy G, Sawaya R. Management of brain metastases: the indispensable role of surgery. J Neurooncol 2009; 92(3):275-82). The incidence of CNS metastasis has increased in recent years, possibly due to prolonged survival of patients given aggressive treatments for their primary disease. Lung and breast cancers are the most common types of primary tumors to develop brain metastases. Brain metastases are present in approximately 10-16% of patients with metastatic disease but large autopsy studies indicate frequencies as high as 18-45% (Al-Shamy G, Sawaya R. Management of brain metastases: the indispensable role of surgery. J Neurooncol 2009; 92(3):275-82; Weil R J, Palmieri D C, Bronder J L, Stark A M, Steeg P S. Breast cancer metastasis to the central nervous system. Am J Pathol 2005; 167(4):913-20; and Sharma M, Abraham J. CNS metastasis in primary breast cancer. Expert Rev Anticancer Ther 2007; 7(11):1561-6). CNS metastases occur rapidly, usually within 2-3 years following diagnosis of metastatic disease, and the median survival from detection of CNS involvement is a stifling 13 months (Al-Shamy G, Sawaya R. Management of brain metastases: the indispensable role of surgery. J Neurooncol 2009; 92(3):275-82).

Metastasis to the CNS remains a major cause of morbidity and mortality in patients with systemic cancers and is a common sanctuary site for patients with breast or lung cancer metastasis. Brain metastases are becoming increasingly prevalent as greater control over systemic disease is achieved. There have been limited improvements in the treatment of brain metastases and current treatment paradigms rely on surgical resection and radiation therapy.

Progress in treating brain metastases has been hampered by a lack of model systems, a lack of human tissue samples, and the exclusion of brain metastatic patients from many clinical trials. Current models are principally derived from cell lines and likely do not represent the human disease. Moreover, there are relatively few therapeutic options for brain/central nervous system metastases beyond surgery and radiation because of the metastases multi-focal nature and association with late-stage disease and other distant manifestations. As such, there is a need to work toward innovative treatment approaches for patients with CNS metastasis and metastases to other locales within the body. The development of preclinical models will be critical for the development of novel therapies and a better understanding of the disease biology. Moreover, the development of preclinical models could have provide useful information regarding predictive biomarkers, preventative measures, and "endpoint" therapies.

SUMMARY

Some embodiments of the invention provide a method of developing a preclinical model of a metastatic cancer. In some aspects, the method includes obtaining samples of a primary tumor and a metastatic tumor from a subject and isolating nucleic acids from portions of the primary and metastatic tumor. The method may also include isolating other biomolecules from the samples, including proteins. The method also provides performing at least one of whole-exome sequencing, whole-gemone sequencing (e.g., long insert whole genome sequencing), and whole-transcriptome sequencing on the nucleic acids isolated from the samples. Thereafter, the method includes determining an allelic status of one or more markers in the samples of the primary and/or metastatic tumors. In some aspects, the methods according the present invention include performing DNA methylation analysis prior to determining the allelic status of the one or more markers.

The method further includes introducing a second portion of the sample of the metastatic tumor into a model organism to create a subject-derived xenograft. The method may also include administering one or more pharmaceutical compositions to the model organism (e.g., a mouse, such as a NOD scid gamma mouse) comprising the subject-derive xenograft. For example, the pharmaceutical compositions are selected based on the allelic status of the one or more markers in the primary tumor or the metastatic tumor. In some embodiments, the sample of the metastatic tumor is orthotopically administered to the model organism or the sample of the metastatic tumor is administered in a flank of the model organism. Some embodiments may also include creating an in vitro cell line using a third portion of the sample of the primary tumor or a third portion the sample of the metastatic tumor. In some aspects, the metastatic tumor can be found in the central nervous system of the subject and the primary tumor can be resected from a region of the subject that includes the breast or the lung.

Some embodiments of the invention provide a method of selecting a pharmaceutical composition to treat a subject with metastatic cancer. For example, the method comprises the steps of: (i) obtaining a sample of a metastatic tumor from the subject; (ii) performing at least one of whole-exome sequencing, whole-gemone sequencing (e.g., long insert whole genome sequencing), and whole-transcriptome sequencing on the sample; (iii) determining an allelic status of one or more markers in the sample; (iv) introducing a portion of the sample into a model organism to create a subject-derived xenograft; (iv) administering one or more pharmaceutical compositions to the model organism comprising the subject-derived xenograft, the one or more pharmaceutical compositions being selected based on the allelic status of the one or more markers in the sample; and (v) assessing growth of the subject-derived xenograft after administration of the one or more pharmaceutical compositions.

Some embodiments of the method include administering the one or more pharmaceutical compositions to the subject if growth of subject-derived xenograft in the model organism is ceased or reduced by the one or more pharmaceutical compositions. Moreover, the method may also include performing DNA methylation analysis prior to determining the allelic status of the one or more markers or creating an in vitro cell line using another portion of the sample of the metastatic tumor. The method may also include obtaining additional samples from the subject, including a whole-blood sample, a primary-tumor sample, a plasma sample, and/or a control sample. The method may also include preserving the additional samples.

Additional objectives, advantages and novel features will be set forth in the description which follows or will become apparent to those skilled in the art upon examination of the drawings and detailed description which follows.

REFERENCE TO COLOR FIGURES

This application contains at least one photograph executed in color. Copies of this patent application publication with color photographs will be provided by the Office upon request and payment of the necessary fee.

BRIEF DESCRIPTION OF THE DRAWINGS

FIG. 2A is a line graph depicting tumor weight change over time in NSG mice (NOD scid gamma mice) that have received a patient-derived xenograft via flank injection.

FIG. 2B is an image of a cell line created from the same patient's metastatic tumor used to create the patient-derived xenograft in FIG. 2A.

FIG. 9 is a chart detailing sample origins and different samples obtained from patients and processing of the samples.

FIG. 10A is a series of copy number variation plots illustrating data generated from the patient's tumor. FIG. 10B is a series of copy number variation plots illustrating data generated from the patient-derived xenografts. FIG. 10C is a series of copy number variation plots illustrating data generated from cell lines generated from the patient's tumor cells. Finally, FIG. 10D is a Venn diagram illustrating the commonality in the copy number variation between the three sample sources.

FIG. 15A is a series of copy number variation plots illustrating data generated from the patient's tumor. FIG. 15B is a series of copy number variation plots illustrating data generated from the patient-derived xenografts. FIG. 15C is a series of copy number variation plots illustrating data generated from cell lines generated from the patient's tumor cells.

The headings used in the figures should not be interpreted to limit the scope of the claims.

DETAILED DESCRIPTION

Some embodiments of the invention provide systems and methods of creating preclinical models of metastases to provide those skilled in the art (e.g., physicians) with a greater understanding of primary cancers and metastases spreading therefrom. Some aspects of the invention include obtaining one or more samples from a patient that has been diagnosed with a primary cancer and a metastasis of the primary cancer to one or more other locations within the patient. By way of example only, embodiments of the invention can be used in creating preclinical models of breast and/or lung cancer that has metastasized to the central nervous system (CNS). In other embodiments, other primary cancers (e.g., pancreatic cancer) and metastases (e.g., bone) can be studied using the systems and methods disclosed herein.

In some embodiments, the invention may include creating in vivo and/or in vitro models of cancer. For example, samples can be obtained from the patient that include portions of a primary tumor and/or a metastatic tumor. Other samples may be obtained by harvesting whole blood. In other embodiments, samples from any other portions of the patient may be encompassed by the invention.

Figure 1:
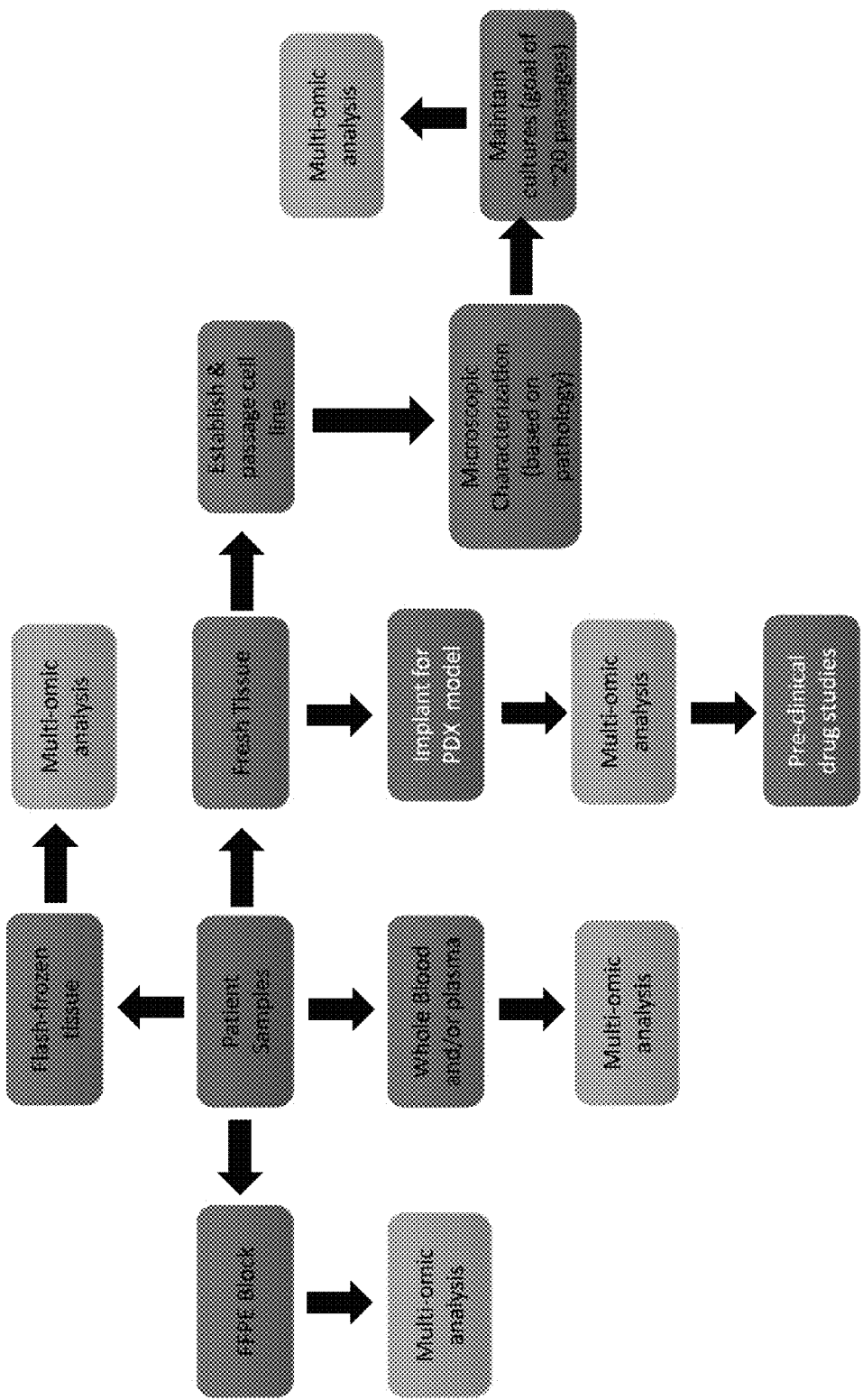
FIG. 1 is a simplified illustration depicting processes of obtaining, preserving, and analyzing samples according to some embodiments of the invention.

As generally illustrated in FIG. 1, in some embodiments, portions of the primary tumor and/or metastatic tumor can be obtained from the patient and preserved (e.g., via flash freezing, storage in nutrient medium and kept cool, formalin-fixed and embedded in a paraffin block, etc.). Thereafter, at least a portion of the samples can be analyzed using one or more molecular techniques to assess any changes in patient's genome (e.g., germline and/or somatic genome), transcriptome, exome, proteome, etc. to make determinations regarding potential therapeutic approaches to treating the patient. For example, determinations of the occurrence of certain alterations in one or more genes (e.g., an allelic status) of the patients may be associated with known therapeutics. In other words, the discovery of one or more types of mutations/alleles can lead treating physicians to treat with one or more therapeutics known to target those mutations/alleles.

In addition to the molecular analyses of the samples, other avenues can be pursued. For example, at least a portion of the primary and/or metastatic tumors can be used to establish one or more in vitro cell lines and/or patient-derived xenografts that can be implanted into model animals (e.g., mice). By creating these models outside of the patient, those skilled in the art can further analyze the molecular characteristics of the primary and/or metastatic tumors to make determinations regarding the origins of the primary and/or metastatic tumors and potential therapeutic options.

Generally, some embodiments of the present invention can be used to identify, quantify, detect, assess, isolate, and/or augment expression levels of one or more markers. A marker may be any molecular structure produced by a cell, expressed inside the cell, accessible on the cell surface, or secreted by the cell. A marker may be any protein, carbohydrate, fatty acid, nucleic acid, catalytic site, or any combination of these such as an enzyme, glycoprotein, cell membrane, virus, a particular cell, or other uni- or multimolecular structure. A marker may be represented by a sequence of a nucleic acid or any other molecules derived from the nucleic acid. Examples of such nucleic acids include miRNA, tRNA, siRNA, mRNA, cDNA, genomic DNA sequences, or complementary sequences thereof. Alternatively, a marker may be represented by a protein sequence. The concept of a marker is not limited to the exact nucleic acid sequence or protein sequence or products thereof, rather it encompasses all molecules that may be detected by a method of assessing the marker. Without being limited by the theory, the detection of the marker may encompass the detection and/or determination of a change in copy number (e.g., copy number of a gene or other forms of nucleic acid), the detection of one or more translocations, the detection of epigenetic changes (e.g., methylation status), the detection of an allele of the one or more markers, etc.

Therefore, examples of molecules encompassed by a marker represented by a particular sequence further include alleles of the gene used as a marker. An allele includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frame shift mutations, single nucleotide polymorphisms (SNPs), inversions, translocations, heterochromatic insertions, and differentially methylated sequences relative to a reference gene, whether alone or in combination.

An allele of a gene/marker may or may not produce a functional protein; may produce a protein with altered function, localization, stability, dimerization, or protein-protein interaction; may have overexpression, under-expression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

Some embodiments of the invention may comprise the use of one or more methods of amplifying a nucleic acid-based starting material (i.e., a template). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as φ29, whole genome PCR, in vitro transcription with T7 RNA polymerase or any other RNA polymerase, or any other method by which copies of a desired sequence are generated.

In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complementary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or non-fluorescent) stain, enzyme, or nonradioactive metal.

Specific examples include, but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethyl-amino-phenylazo)benzoic acid ("Dabcyl"); 4-(4'-dimethyl-amino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR facilitating the reading of the target amplification.

Either primers or primers along with probes allow a quantification of the amount of specific template DNA present in the initial sample. In addition, RNA may be detected by PCR analysis by first creating a DNA template from RNA through a reverse transcriptase enzyme. The marker expression may be detected by quantitative PCR analysis facilitating genotyping analysis of the samples.

An illustrative example, using dual-labeled oligonucleotide probes in PCR reactions is disclosed in U.S. Pat. No. 5,716,784 to DiCesare. In one example of the PCR step of the multiplex Real Time-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Examples of apparatus suitable for detection include, e.g. Applied Biosystems™ 7900HT real-time PCR platform and Roche's 480 LightCycler, the ABI Prism 7700 sequence detector using 96-well reaction plates or GENEAMP PC System 9600 or 9700 in 9600 emulation mode followed by analysis in the ABA Prism Sequence Detector or TAQMAN LS-50B PCR Detection System. The labeled probe facilitated multiplex Real Time-PCR/PCR can also be performed in other real-time PCR systems with multiplexing capabilities.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "template" refers to nucleic acid originating from a sample that is analyzed for the presence of a marker of interest. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "PCR fragment," and "amplification product" refer to the resultant mixture of compounds after two or more cycles of the PCR steps of denaturation, annealing and extension. These terms encompass the case where there has been amplification of one or more segments of one or more target sequences.

In some forms of PCR assays, quantification of a target in an unknown sample is often required. Such quantification is often in reference to the quantity of a control sample. The control sample DNA may be co-amplified in the same tube in a multiplex assay or may be amplified in a separate tube. Generally, the control sample contains DNA at a known concentration. The control sample DNA may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

The algorithm for Ct values in real time-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

An oligonucleotide may be any polynucleotide of at least 2 nucleotides. Oligonucleotides may be less than 10, 15, 20, 30, 40, 50, 75, 100, 200, or 500 nucleotides in length. While oligonucleotides are often linear, they may assume a circular or other two dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. In some aspects of the invention, an oligonucleotide may be 2 to 1000 bases in length. In other aspects, it may be 5 to 500 bases in length, 5 to 100 bases in length, 5 to 50 bases in length, or 10 to 30 bases in length. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

As used herein, a "whole genome sequence", or WGS (also referred to in the art as a "full", "complete", or "entire" genome sequence), or similar phraseology is to be understood as encompassing a substantial, but not necessarily complete, genome of a subject. In the art the term "whole genome sequence" or WGS is used to refer to a nearly complete genome of the subject, such as at least 95% complete in some usages. The term "whole genome sequence" or WGS as used herein does not encompass "sequences" employed for gene-specific techniques such as single nucleotide polymorphism (SNP) genotyping, for which typically less than 0.1% of the genome is covered. The term "whole genome sequence", or WGS as used herein does not require that the genome be aligned with any reference sequence, and does not require that variants or other features be annotated.

As used herein the term "whole genome sequencing" refers to determining the complete DNA sequence of the genome at one time.

As used herein the term "whole exome sequencing" refers to selective sequencing of coding regions of the DNA genome. The targeted exome is usually the portion of the DNA that translate into proteins, however regions of the exome that do not translate into proteins may also be included within the sequence.

As used herein the term "whole transcriptome sequencing" refers to determining the expression of all RNA molecules including messenger RNA (mRNA), ribosomal RNA (rRNA), transfer RNA (tRNA), and non-coding RNA.

As used herein the term "high-throughput screening" refers to a method for scientific experimentation especially relevant to the fields of biology and chemistry. Through a combination of modern robotics and other specialized laboratory hardware, it allows a researcher to effectively screen large amounts of samples simultaneously.

As used herein, the term "long insert whole genome sequencing" refers to the sequencing process detailed in W. Liang et al., *Long Insert Whole Genome Sequencing For Copy Number Variant and Translocation Detection*, Nucleic Acids Research 42 e8 (2014), which is hereby incorporated by reference for all purposes.

As used here in the term "library" is used in its art-recognized sense, that is a collection of nucleic acid molecules (RNA, cDNA or genomic DNA) obtained from a particular source being studied, such as a certain differentiated cell, or a cell representing a certain species (e.g., human).

As used herein, the phrase "next generation sequencing" refers to sequencing technologies having increased throughput as compared to traditional Sanger- and capillary electrophoresis-based approaches, for example with the ability to generate hundreds of thousands or millions of relatively small sequence reads at a time. Some examples of next generation sequencing techniques include, but are not limited to, sequencing by synthesis, sequencing by ligation, and sequencing by hybridization. Examples of next generations sequencing methods include pyrosequencing as used by 454 Corporation, Illumina's Solexa system, the SOLiD™ (Sequencing by Oligonucleotide Ligation and Detection) system (Life Technologies Inc.), and on Torrent Sequencing systems such as the Personal Genome Machine or the Proton Sequencer (Life Technologies Inc).

In some embodiments, the biological samples are analyzed by Sequencing by Synthesis (SBS) techniques. As used herein, SBS techniques can be understood to refer to next-generation sequencing techniques. SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. However, in some of the methods described herein, more than one type of nucleotide monomer can be provided to a target nucleic acid in the presence of a polymerase in a delivery.

SBS can utilize nucleotide monomers that have a terminator moiety or those that lack any terminator moieties. Methods utilizing nucleotide monomers lacking terminators include, for example, pyrosequencing and sequencing using γ-phosphate-labeled nucleotides. In methods using nucleotide monomers lacking terminators, the number of different nucleotides added in each cycle can be dependent upon the template sequence and the mode of nucleotide delivery. For SBS techniques that utilize nucleotide monomers having a terminator moiety, the terminator can be effectively irreversible under the sequencing conditions used as is the case for traditional Sanger sequencing which utilizes dideoxynucleotides, or the terminator can be reversible as is the case for sequencing methods developed by Solexa (now Illumina, Inc.). In preferred methods a terminator moiety can be reversibly terminating.

SBS techniques can utilize nucleotide monomers that have a label moiety or those that lack a label moiety. Accordingly, incorporation events can be detected based on a characteristic of the label, such as fluorescence of the label; a characteristic of the nucleotide monomer such as molecular weight or charge; a byproduct of incorporation of the nucleotide, such as release of pyrophosphate; or the like. In embodiments, where two or more different nucleotides are present in a sequencing reagent, the different nucleotides can be distinguishable from each other, or alternatively, the two or more different labels can be the indistinguishable under the detection techniques being used. For example, the different nucleotides present in a sequencing reagent can have different labels and they can be distinguished using appropriate optics as exemplified by the sequencing methods developed by Solexa (now Illumina, Inc.). However, it is also possible to use the same label for the two or more different nucleotides present in a sequencing reagent or to use detection optics that do not necessarily distinguish the different labels. Thus, in a doublet sequencing reagent having a mixture of A/C both the A and C can be labeled with the same fluorophore. Furthermore, when doublet delivery methods are used all of the different nucleotide monomers can have the same label or different labels can be used, for example, to distinguish one mixture of different nucleotide monomers from a second mixture of nucleotide monomers. For example, using the [First delivery nucleotide monomers]+[Second delivery nucleotide monomers] nomenclature set forth above and taking an example of A/C+(1/T), the A and C monomers can have the same first label and the G and T monomers can have the same second label, wherein the first label is different from the second label. Alternatively, the first label can be the same as the second label and incorporation events of the first delivery can be distinguished from incorporation events of the second delivery based on the temporal separation of cycles in an SBS protocol. Accordingly, a low resolution sequence representation obtained from such mixtures will be degenerate for two pairs of nucleotides (T/G, which is complementary to A and C, respectively; and C/A which is complementary to G/T, respectively).

Some embodiments include pyrosequencing techniques. Pyrosequencing detects the release of inorganic pyrophosphate (PPi) as particular nucleotides are incorporated into the nascent strand (Ronaghi, M., Karamohamed, S., Pettersson, B., Uhlen, M. and Nyren, P. (1996) "Real-time DNA sequencing using detection of pyrophosphate release." Analytical Biochemistry 242(1), 84-9; Ronaghi, M. (2001) "Pyrosequencing sheds light on DNA sequencing." Genome Res. 11(1), 3-11; Ronaghi, M., Uhlen, M. and Nyren, P. (1998) "A sequencing method based on real-time pyrophosphate." Science 281(5375), 363; U.S. Pat. Nos. 6,210,891; 6,258,568 and 6,274,320, the disclosures of which are incorporated herein by reference in their entireties). In pyrosequencing, released PPi can be detected by being immediately converted to adenosine triphosphate (ATP) by ATP sulfurylase, and the level of ATP generated is detected via luciferase-produced photons.

In another example type of SBS, cycle sequencing is accomplished by stepwise addition of reversible terminator nucleotides containing, for example, a cleavable or photobleachable dye label as described, for example, in U.S. Pat. Nos. 7,427,673, 7,414,113 and 7,057,026, the disclosures of which are incorporated herein by reference. This approach is being commercialized by Solexa (now Illumina Inc.), and is also described in WO 91/06678 and WO 07/123,744 (filed in the United States Patent and Trademark Office as U.S. Ser. No. 12/295,337), each of which is incorporated herein by reference in their entireties. The availability of fluorescently-labeled terminators in which both the termination can be reversed and the fluorescent label cleaved facilitates efficient cyclic reversible termination (CRT) sequencing. Polymerases can also be co-engineered to efficiently incorporate and extend from these modified nucleotides.

In other embodiments, Ion Semiconductor Sequencing is utilized to analyze the purified small fragments of DNA from the sample. Ion Semiconductor Sequencing is a method of DNA sequencing based on the detection of hydrogen ions that are released during DNA amplification. This is a method of "sequencing by synthesis," during which a complementary strand is built based on the sequence of a template strand.

For example, a microwell containing a template DNA strand to be sequenced can be flooded with a single species of deoxyribonucleotide (dNTP). If the introduced dNTP is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple dNTP molecules will be incorporated in a single cycle. This leads to a corresponding number of released hydrogens and a proportionally higher electronic signal.

This technology differs from other sequencing technologies in that no modified nucleotides or optics are used. Ion semiconductor sequencing may also be referred to as ion torrent sequencing, pH-mediated sequencing, silicon sequencing, or semiconductor sequencing. Ion semiconductor sequencing was developed by Ion Torrent Systems Inc. and may be performed using a bench top machine. Rusk, N. (2011). "Torrents of Sequence," Nat Meth 8(1): 44-44. Although it is not necessary to understand the mechanism of an invention, it is believed that hydrogen ion release occurs during nucleic acid amplification because of the formation of a covalent bond and the release of pyrophosphate and a charged hydrogen ion. Ion semiconductor sequencing exploits these facts by determining if a hydrogen ion is released upon providing a single species of dNTP to the reaction.

For example, microwells on a semiconductor chip that each contain one single-stranded template DNA molecule to be sequenced and one DNA polymerase can be sequentially flooded with unmodified A, C, G or T dNTP. Pennisi, E. (2010). "Semiconductors inspire new sequencing technologies" Science 327(5970): 1190; and Perkel, J., "Making contact with sequencing's fourth generation" Biotechniques (2011). The hydrogen ion that is released in the reaction changes the pH of the solution, which is detected by a hypersensitive ion sensor. The unattached dNTP molecules are washed out before the next cycle when a different dNTP species is introduced.

Beneath the layer of microwells is an ion sensitive layer, below which is a hypersensitive ISFET ion sensor. All layers are contained within a CMOS semiconductor chip, similar to that used in the electronics industry. Each released hydrogen ion triggers the ISFET ion sensor. The series of electrical pulses transmitted from the chip to a computer is translated into a DNA sequence, with no intermediate signal conversion required. Each chip contains an array of microwells with corresponding ISFET detectors. Because nucleotide incorporation events are measured directly by electronics, the use of labeled nucleotides and optical measurements are avoided.

An example of a Ion Semiconductor Sequencing technique suitable for use in the methods of the provided disclosure is Ion Torrent sequencing (U.S. Patent Application Numbers 2009/0026082, 2009/0127589, 2010/0035252, 2010/0137143, 2010/0188073, 2010/0197507, 2010/0282617, 2010/0300559, 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and are attached at a resolution such that the fragments are individually resolvable. Addition of one or more nucleotides releases a proton (H+), which signal detected and recorded in a sequencing instrument. The signal strength is proportional to the number of nucleotides incorporated. User guides describe in detail the Ion Torrent protocol(s) that are suitable for use in methods of the invention, such as Life Technologies' literature entitled "Ion Sequencing Kit for User Guide v. 2.0" for use with their sequencing platform the Personal Genome Machine™ (PCG).

In some embodiments, as a part of the sample preparation process, "barcodes" may be associated with each sample. In this process, short oligos are added to primers, where each different sample uses a different oligo in addition to a primer.

Some embodiments of the invention may include assessing, determining, quantifying, or altering the expression of a marker. As used herein expression encompasses any and all processes through which material derived from a nucleic acid template may be produced. Expression thus includes RNA transcription, mRNA splicing, protein translation, protein folding, post-translational modification, membrane transport, associations with other molecules, addition of carbohydrate moieties to proteins, phosphorylation, protein complex formation and any other process along a continuum that results in biological material derived from genetic material. Expression also encompasses all processes through which the production of material derived from a nucleic acid template may be actively or passively suppressed. Such processes include all aspects of transcriptional and translational regulation. Examples include heterochromatic silencing, transcription factor inhibition, any form of RNAi silencing, microRNA silencing, small interfering RNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, next-generation sequencing, including whole or partial transcriptome sequencing, or any other method of detecting a specific nucleic acid now known or yet to be disclosed. Other examples include any process of assessing expression that uses an antibody including the following nonlimiting examples, flow cytometry, immunohistochemistry, ELISA, Western blot, and immunoaffinity chromatography. Antibodies may be monoclonal, polyclonal, or any antibody fragment including an Fab, F(ab)2, Fv, scFv, phage display antibody, peptibody, multispecific ligand, or any other reagent with specific binding to a marker. Such methods also include direct methods used to assess protein expression including the following nonlimiting examples: HPLC, mass spectrometry, protein microarray analysis, PAGE analysis, isoelectric focusing, 2-D gel electrophoresis, and enzymatic assays. Samples from which expression may be detected include single cells, whole organs or any fraction of a whole organ, whether in vitro, ex vivo, in vivo, or post-mortem.

Other methods used to assess expression include the use of natural or artificial ligands capable of specifically binding one or more markers, including a protein, carbohydrate, fat, nucleic acid, catalytic site, or any combination of these such as an enzyme, glycoprotein, cell membrane, virus, cell, organ, organelle, or any uni- or multimolecular structure that constitutes a marker that may be specifically bound by a ligand. Such ligands include antibodies, antibody complexes, conjugates, natural ligands, small molecules, nanoparticles, or any other molecular entity capable of specific binding to a marker. Ligands may be associated with a label such as a radioactive isotope or chelate thereof, dye (fluorescent or nonfluorescent,) stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Positive expression encompasses any difference between a cell expressing markers and a cell that does not express one or more of the markers. The exact nature of positive expression varies by the method, but is well known to those skilled in the art of practicing a particular method. Positive expression may be assessed by a detector, an instrument containing a detector, or by aided or unaided human eye. Examples include but are not limited to specific staining of cells expressing a target in an IHC slide, binding of RNA from a sample to a microarray and detection of binding through the use of said microarray, a particular rate of dye incorporation in real-time RTPCR measured in ΔCt or alternatively in the number of PCR cycles necessary to reach a particular optical density at a wavelength at which a double stranded DNA binding dye (e.g. SYBR Green) incorporates, through release of label from a previously labeled reporter probe used in a real-time RTPCR reaction, detection of fluorescence on a cell expressing a target by a flow cytometer, the presence of radiolabeled bands on film in a Northern blot, detection of labeled blocked RNA by RNAse protection assay, cell death measured by apoptotic markers, cell death measured by shrinkage of a tumor, or any other signal for the expression of a marker in existence now or yet to be developed. In some aspects of the invention, positive expression is a sufficient level of expression to correlate with a particular response such as susceptibility to cancer recurrence.

In some aspects of the invention, reduced expression constitutes no detectable expression. However, the concept of reduced expression further encompasses insufficient expression to reach or exceed a threshold, cutoff, or level that has been previously shown to result in a particular cellular or physiological response. Reduced expression may include similar expression relative to a control that has been previously determined not to express the marker(s) or similar expression to a control that has been previously determined not to exhibit the response. In this case, even though expression may be detectable, it still constitutes reduced expression. In some aspects of the invention, an expression level of a marker in a control known to have a reduced or increase risk of recurrence is predetermined and expression similar to that level is correlated with reduced or increase risk of recurrence. Increased or reduced expression includes expression that is 75% 50%, 25%, 10%, 5%, 1%, 0.1%, greater or less of that of a control cell or a median level of expression in a population. Reduced expression may also include greater than or less than $1\times10^{-5}$ greater or less expression normalized to the expression of a housekeeping gene.

The invention contemplates assessing the expression of the marker(s) in any biological sample from which the expression may be assessed. One skilled in the art would know to select a particular biological sample and how to collect said sample depending upon the marker that is being assessed. Examples of sources of samples include but are not limited to biopsy or other in vivo or ex vivo analysis of prostate, breast, skin, muscle, fascia, brain, endometrium, lung, head and neck, pancreas, small intestine, blood, liver, testes, ovaries, colon, skin, stomach, esophagus, spleen, lymph node, bone marrow, kidney, placenta, or fetus. In some aspects of the invention, the sample comprises a fluid sample, such as peripheral blood, lymph fluid, ascites, serous fluid, pleural effusion, sputum, cerebrospinal fluid, amniotic fluid, lacrimal fluid, stool, or urine. In one aspect of the invention, the sample comprises primary or metastatic tumor cells. For example, cells from primary lung or breast tumor and/or cells from a metastatic tumor from the CNS, bone, blood, etc.

Assessing the risk of a particular disease outcome includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

The sample in this method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues.

The term "subject" is used in its broadest sense. In a preferred embodiment, the subject is a mammal. Non-limiting examples of mammals include humans, dogs, cats, horses, cows, sheep, goats, and pigs. Preferably, a subject includes any human or non-human mammal, including for example: a primate, cow, horse, pig, sheep, goat, dog, cat, or rodent, capable of developing cancer including human patients that are suspected of having cancer, that have been diagnosed with cancer, or that have a family history of cancer.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

Methods for evaluation of DNA methylation are well known. For example, Laird (2010) Nature Reviews Genetics 11: 191-203 provides a review of DNA methylation analysis. In some embodiments, methods for evaluating methylation include randomly shearing or randomly fragmenting the genomic DNA, cutting the DNA with a methylation-dependent or methylation-sensitive restriction enzyme and subsequently selectively identifying and/or analyzing the cut or uncut DNA. Selective identification can include, for example, separating cut and uncut DNA (e.g., by size) and quantifying a sequence of interest that was cut or, alternatively, that was not cut. See, e.g., U.S. Pat. No. 7,186,512. In some embodiments, the method can encompass amplifying intact DNA after restriction enzyme digestion, thereby only amplifying DNA that was not cleaved by the restriction enzyme in the area amplified. See, e.g., U.S. patent application Ser. Nos. 10/971,986; 11/071,013; and 10/971,339. In some embodiments, amplification can be performed using primers that are gene specific. Alternatively, adaptors can be added to the ends of the randomly fragmented DNA, the DNA can be digested with a methylation-dependent or methylation-sensitive restriction enzyme, intact DNA can be amplified using primers that hybridize to the adaptor sequences. In some embodiments, a second step can be performed to determine the presence, absence or quantity of a particular gene in an amplified pool of DNA. In some embodiments, the DNA is amplified using real-time, quantitative PCR.

In some embodiments, the methods comprise quantifying the average methylation density in a target sequence within a population of genomic DNA. In some embodiments, the method comprises contacting genomic DNA with a methylation-dependent restriction enzyme or methylation-sensitive restriction enzyme under conditions that allow for at least some copies of potential restriction enzyme cleavage sites in the locus to remain uncleaved; quantifying intact copies of the locus; and comparing the quantity of amplified product to a control value representing the quantity of methylation of control DNA, thereby quantifying the average methylation density in the locus compared to the methylation density of the control DNA.

The quantity of methylation of a locus of DNA can be determined by providing a sample of genomic DNA comprising the locus, cleaving the DNA with a restriction enzyme that is either methylation-sensitive or methylation-dependent, and then quantifying the amount of intact DNA or quantifying the amount of cut DNA at the DNA locus of interest. The amount of intact or cut DNA will depend on the initial amount of genomic DNA containing the locus, the amount of methylation in the locus, and the number (i.e., the fraction) of nucleotides in the locus that are methylated in the genomic DNA. The amount of methylation in a DNA locus can be determined by comparing the quantity of intact DNA or cut DNA to a control value representing the quantity of intact DNA or cut DNA in a similarly-treated DNA sample. The control value can represent a known or predicted number of methylated nucleotides. Alternatively, the control value can represent the quantity of intact or cut DNA from the same locus in another (e.g., normal, non-diseased) cell or a second locus.

By using methylation-sensitive or methylation-dependent restriction enzyme under conditions that allow for at least some copies of potential restriction enzyme cleavage sites in the locus to remain uncleaved and subsequently quantifying the remaining intact copies and comparing the quantity to a control, average methylation density of a locus can be determined. If the methylation-sensitive restriction enzyme is contacted to copies of a DNA locus under conditions that allow for at least some copies of potential restriction enzyme cleavage sites in the locus to remain uncleaved, then the remaining intact DNA will be directly proportional to the methylation density, and thus may be compared to a control to determine the relative methylation density of the locus in the sample. Similarly, if a methylation-dependent restriction enzyme is contacted to copies of a DNA locus under conditions that allow for at least some copies of potential restriction enzyme cleavage sites in the locus to remain uncleaved, then the remaining intact DNA will be inversely proportional to the methylation density, and thus may be compared to a control to determine the relative methylation density of the locus in the sample. Such assays are disclosed in, e.g., U.S. patent application Ser. No. 10/971,986. In some embodiments, quantitative amplification methods (e.g., quantitative PCR or quantitative linear amplification) can be used to quantify the amount of intact DNA within a locus flanked by amplification primers following restriction digestion. Methods of quantitative amplification are disclosed in, e.g., U.S. Pat. Nos. 6,180,349; 6,033,854; and 5,972,602, as well as in, e.g., Gibson et al., Genome Research 6:995-1001 (1996); DeGraves et al., Biotechniques 34(1): 106-10, 112-5 (2003); Deiman B et. al., Mol Biotechnol. 20(2): 163-79 (2002).

Additional methods for detecting DNA methylation can involve genomic sequencing before and after treatment of the DNA with bisulfite. See, e.g., Frommer et al., Proc. Natl. Acad. Sci. USA 89: 1827-1831 (1992). When sodium bisulfite is contacted to DNA, unmethylated cytosine is converted to uracil, while methylated cytosine is not modified.

In some embodiments, restriction enzyme digestion of PCR products amplified from bisulfite-converted DNA is used to detect DNA methylation. See, e.g., Sadri & Hornsby, Nucl. Acids Res. 24:5058-5059 (1996); Xiong & Laird, Nucleic Acids Res. 25:2532-2534 (1997).

Cancer cells include any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Examples of cancers that could serve as sources of cancer cells include solid tumors such as fibrosarcoma, myxosarcoma, liposarcoma, chondrosarcoma, osteogenic sarcoma, chordoma, angiosarcoma, endothelia sarcoma, lymphangiosarcoma, lymphangioendothelio sarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell king carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells include blood borne cancer, such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

The present invention further provides kits to be used in assessing the expression of a marker in a subject to assess the risk of developing disease, diagnosing the subject as having a stage of the disease, or determining to which stage the disease has progressed. Kits include any combination of components that facilitates the performance of an assay. A kit that facilitates assessing the expression of the markers may include suitable nucleic acid-based and immunological reagents as well as suitable buffers, control reagents, and printed protocols.

Kits that facilitate nucleic acid based methods may further include one or more of the following: specific nucleic acids such as oligonucleotides, labeling reagents, enzymes including PCR amplification reagents such as Taq or Pfu, reverse transcriptase, or other, and/or reagents that facilitate hybridization, as previously described.

In some aspects of the invention, a probe may be affixed to a solid substrate. In other aspects of the invention, the sample may be affixed to a solid substrate. A probe or sample may be covalently bound to the substrate or it may be bound by some non-covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi-solid material onto which a probe may be affixed, attached or printed, either singly or in the formation of a microarray. Examples of substrate materials include but are not limited to polyvinyl, polystyrene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array. The sample may be bound to a substrate in the case of a Southern Blot.

Some embodiments of the invention may include the administration of a pharmaceutical composition or a pharmacological composition to a subject that has been diagnosed with cancer. Such pharmaceutical compositions may take any physical form necessary depending on a number of factors including the desired method of administration and the physicochemical and stereochemical form taken by the compound or pharmaceutically acceptable salts of the compound. Such physical forms include a solid, liquid, gas, sol, gel, aerosol, or any other physical form now known or yet to be disclosed.

The concept of a pharmaceutical composition encompasses a compound or a pharmaceutically acceptable salt thereof with or without any other additive. The physical form of the invention may affect the route of administration and one skilled in the art would know to choose a route of administration that takes into consideration both the physical form of the compound and the disorder to be treated. Pharmaceutical compositions that include the compound may be prepared using methodology well known in the pharmaceutical art. A pharmaceutical composition that includes the disclosed compound may include a second effective compound of a distinct chemical formula from the disclosed compound. This second effective compound may have the same or a similar molecular target as the target or it may act upstream or downstream of the molecular target of the compound with regard to one or more biochemical pathways.

Pharmaceutical compositions include materials capable of modifying the physical form of a dosage unit. In one nonlimiting example, the composition includes a material that forms a coating that contains the compound. Materials that may be used in a coating, include, for example, sugar, shellac, gelatin, or any other inert coating agent.

Pharmaceutical compositions including the disclosed compound may be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single phase, bi-phasic, or multi-phasic systems.

In some aspects of the invention, the pharmaceutical composition including the disclosed compound is in the form of a solvate. Such solvates are produced by the dissolution of the disclosed compound in a pharmaceutically acceptable solvent. Pharmaceutically acceptable solvents include any mixtures of one or more solvents. Such solvents may include pyridine, chloroform, propan-1-ol, ethyl oleate, ethyl lactate, ethylene oxide, water, ethanol, and any other solvent that delivers a sufficient quantity of the disclosed compound to treat the indicated condition.

Pharmaceutical compositions may also include at least one pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, and oils (including petroleum, animal, vegetable or synthetic oils.) Such carriers include particulates such as a tablet or powder, liquids such as oral syrup or injectable liquid, and inhalable aerosols. Further examples include saline, gum *acacia*, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or diglycerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers and formulations are well known in the art.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intramsal, intracerebral, intraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include the use of an inhaler or nebulizer, formulation with an aerosolizing agent, or via perfusion in a fluorocarbon or synthetic pulmonary surfactant. Compounds may be delivered in the context of a vesicle such as a liposome or any other natural or synthetic vesicle. Additional examples of suitable modes of administration are well known in the art.

A pharmaceutical composition formulated to be administered by injection may be prepared by dissolving the disclosed compound with water so as to form a solution. In addition, a surfactant may be added to facilitate the formation of a homogeneous solution or suspension.

Surfactants include any complex capable of non-covalent interaction with the disclosed compound so as to facilitate dissolution or homogeneous suspension of the compound.

Pharmaceutical compositions may be prepared in a form that facilitates topical or transdermal administration. Such preparations may be in the form of a solution, emulsion, ointment, gel base, transdermal patch or iontophoresis device. Examples of bases used in such compositions include opetrolatum, lanolin, polyethylene glycols, beeswax, mineral oil, diluents such as water and alcohol, and emulsifiers and stabilizers, thickening agents, or any other suitable base now known or yet to be disclosed.

Determination of an effective amount of the disclosed compound is within the capability of those skilled in the art, especially in light of the detailed disclosure provided herein. The effective amount of a pharmaceutical composition used to affect a particular purpose as well as its toxicity, excretion, and overall tolerance may be determined in vitro, or in vivo, by pharmaceutical and toxicological procedures either known now by those skilled in the art or by any similar method yet to be disclosed. One example is the in vitro determination of the $IC_{50}$ (half maximal inhibitory concentration) of the pharmaceutical composition in cell lines or target molecules. Another example is the in vivo determination of the $LD_{50}$ (lethal dose causing death in 50% of the tested animals) of the pharmaceutical composition. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for administration also includes the determination of an effective therapeutic amount and a pharmaceutically acceptable dose, including the formulation of an effective dose range for use in vivo, including in humans.

Treatment of a condition or disease is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease. Generally, the effectiveness of treatment is determined by comparing treated groups with non-treated groups.

The addition of a therapeutically effective amount of a compound encompasses any method of dosing of a compound. Dosing of the disclosed compound may include single or multiple administrations of any of a number of pharmaceutical compositions that include the disclosed compound as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A dosing regimen including the regularity of and mode of administration will be dependent on any of a number of factors including but not limited to the subject being treated; the severity of the condition; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions may be administered prior to, concurrently with, or after administration of additional or second pharmaceutical compositions. Concurrent administration means compositions are administered within about one minute of each other. If not administered concurrently, the additional or second pharmaceutical compositions may be administered a period of one or more minutes, hours, days, weeks, or months before or after the pharmaceutical composition that includes the currently disclosed compound. Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration. Cycling therapy may be used, for example, to reduce the development of resistance to one or more of the compositions, to avoid or reduce the side effects of one or more of the compositions, and/or to improve the efficacy of the treatment.

The invention further encompasses kits that facilitate the administration of the disclosed compound to a diseased entity. An example of such a kit includes one or more unit dosages of one or more active ingredients. The unit dosage would be enclosed in a preferably sterile container and would be comprised of the compound and a pharmaceutically acceptable carrier. In another aspect, the unit dosage would comprise one or more lyophilates of the compound. In this aspect of the invention, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the invention, the device comprises the container that encloses the unit dosage. In another aspect, the kit may include one or more additional compounds for administration and administration instructions therefor.

EXAMPLES

Materials and Methods

Identification of Participants

Participants were recruited through contact with clinical collaborators when they presented for tumor resection of lung or breast cancer metastasis.

Participant Samples

Participant samples for this study included blood and resected tumor tissue.

Peripheral Blood

Two 8-10 ml blood samples were collected from participants who had been diagnosed with a metastasis of lung or breast cancer. If a subject received a clinically indicated blood draw, blood collection for this study occurred at the same time. However, some subjects required a research-specific blood draw, if they were not scheduled for a clinical blood draw. Preferred vacutainers (containing anticoagulants) were purple top-EDTA; however, additional types were considered, depending on the type of vacutainers available at the collection site. The blood samples were used to extract plasma and the buffy coat. The tubes were drawn, mixed, and then allowed to sit in a vertical position for thirty minutes. The tubes were then spun for 10-20 minutes at 1100-1300 g using a centrifuge at the clinical site. The plasma was transferred from the tube using an appropriate transfer pipette into 1 ml cryovials, followed by the buffy coat. The coded cryovials were stored in a −80 degree freezer or on dry ice until shipment. Samples were shipped overnight on dry ice to a research institute.

Fresh Tissue Collection 120-130 mg tumor samples were collected from participants who have been diagnosed with a metastasis of lung or breast cancer. A 20-30 mg piece was flash-frozen in liquid nitrogen and used for genomic profiling of original tumor. The remainder was kept fresh and placed in tissue culture medium. All coded samples were shipped at the earliest possible convenience (next day delivery). The 20-30 mg piece was shipped frozen on dry ice, while the remaining tissue was shipped on ice in the culture medium.

FFPE Tissue Collection

Formalin fixed paraffin embedded (FFPE) tissue samples from the primary tumor and metastatic tumor were collected if available. A tissue microarray was constructed dependent on the diameter size used by removing two to four 1.0 mm diameter cores and embedding the cores in a donor block. In addition to the cores, the researchers collected one unstained section at 5 micron thickness for performing an hematoxylin and eosin (H&E) stain followed by two 50-60 micron "scrolls" from the block.

For research purposes, it was preferable to have thick scrolls, as collection of scrolls is less damaging to the cell nuclei, yielding a higher quality DNA sample due to a greater number of fully intact cell nuclei. FFPE blocks or scrolls and the 5 micron section slide were sent prior to commencement of any research from the medical centers storing the biospecimens.

Clinical Data Collection

In addition to basic demographic data, information was collected on the patient's then-current medications, laboratory tests, and details about any surgical procedures or treatments. A medical history form or a de-identified copy of the participant's medical records included the following clinical and medical information from each participant: year of birth, race, ethnicity, or any additional medical information related to the patient. These forms also requested clinical information, including previous genetic testing and treatment course information.

All clinical data was assigned a non-identifying study-specific code before shipment. All information requested was subject to IRB review and abided by guidelines set forth by the 1996 Health Insurance Portability and Accountability Act (HIPAA) to protect the privacy and rights of study participants.

Schedule of Events (i) Participants were consented into the study by the clinical collaborator after they were found to meet the entry criteria for this study. (ii) The clinical staff scheduled a blood draw for the participant. If a participant was receiving a clinically indicated blood draw, blood collection for this study occurred at the same time. (iii) Two 8-10 ml blood samples were collected in a purple-top EDTA vacutainer. (iv) Tissue specimens were obtained through surgery and divided by weight into a 20-30 mg section and a 100 mg section. (v) The 20-30 mg section was placed in liquid nitrogen immediately upon resection. Annotation of time from surgical removal to freeze was provided from each sample. (vi) The 100 mg section was placed in culture medium and shipped on ice for immediate implantation into animals. (vii) All blood and tissue samples were shipped overnight.

Laboratory Methods

The main procedures that were performed on these samples were initial DNA and/or RNA extraction methods using standard nucleic acid extraction procedures, and the creation of xenografts. A variety of molecular analyses were then performed on these nucleic acid samples. The primary genotyping analyses used Affymetrix SNP arrays, ABI microsatellite markers, Next-Generation Sequencing, and Sequenom SNP markers. Sequencing and expression profiling was also be performed on the samples.

Implantation of Primary Tissue for Xenograft Expansion

Immediately after surgical removal, fresh tissue was collected for heterotopic (flank) injection into NSG mice (NOD scid gamma mice—or mice that are on a NOD/ShiLtJ background with severe combined immune deficiency mutation and the IL2 receptor gamma chain deficiency). Excised patient tissue was placed in a culture dish with medium and minced into small pieces, such that minced tissue suspensions could be drawn through a 16-gauge needle. Minced tissues were placed in a conical tube, media was withdrawn, and matrigel was added to the wet tissue in a 1:1 volume ratio. Approximately 200 μl of the matrigel-tissue mixture was injected subcutaneously into the flanks of two to four mice, and tumors were allowed to develop until the tumors achieved a length of 1.0 to 2.0 cm in the longest dimension. Mice were then sacrificed by $CO_2$ asphyxiation, and their flank tumors were immediately excised. Portions of each excised flank tumor were archived as frozen tissue and as paraffin-embedded tissue following formalin fixation. The remainder of each tumor was dispersed in DMEM, processed as described above and passed by injection into the flank of another NSG mouse.

Orthotopic Xenografts of CNS Metastasis for Therapy Testing

Flank tumor xenografts were harvested, mechanically disaggregated, and grown in short-term cell culture (5-14 days) in essential medium. Cells were harvested by trypsinization and injected into the lower lobe of anesthetized mice. Just before treatment initiation, animals were randomized to treatment groups of 10 mice. Typically tumors were established by 1 week, and grew to 1 cm by 4 weeks. Small-inhibitory therapy was initiated 2 weeks after injection.

Xenograft Testing of Novel and Conventional Chemotherapeutic Agents

Mice bearing the orthotopic tumors were randomly assigned to two groups at implantation (n=10 per group): control and drug dose group. Drug was administered orally, intravenously, or intraperitonealy on the day of tumor cell implantation and continued for four-to-six weeks.

Immunohistochemistry (IHC)

Sections were mounted onto a glass slide and stained with reagents designed to detect proteins of interest by IHC staining. This allows samples of many or all of the tumor specimens to be stained at one time. IHC staining was performed to determine the presence or absence of specific proteins and was used to validate potential targets discovered by genome-wide experiments (as previously described).

RNA-Sequencing

Experiments also included RNA-sequencing (RNA-seq) to generate gene and exon level expression profiles. RNA-seq was utilized to quantify the level of gene expression and alternative splicing; transcript annotation; and discovery of transcribed variations. Integration of RNA-Seq and whole exome sequencing (WES) data allowed investigators to study allele-specific expression (exome+RNA-seq).

Primary Cell Line Creation

Sample permitting, fresh tissue was mechanically and enzymatically dissociated and placed into cell culture under multiple conditions for the purpose of analysis and fibroblast cell line establishment. The cell lines were used for various follow-up testing in order to understand the cell biology of the condition.

Establishment of Primary Cell Culture from Fresh Patient Tumor

The tumor tissue was seeded into several T-25 or T-75 Primaria flasks, depending on the amount of tissues available in the sample provided from the patient. In some procedures, multiple types of media were used, with the tumor cells being split into different conditions/flasks containing different media (i.e., to determine which media will provide sufficient growth conditions for the tumor cells).

If the tissue is provided in one piece, the tissue was minced into fine pieces with sterile scalpels, including the removal of any tissue that appears to be potentially stromal or vascular, with a small piece placed in each flask. Thereafter, the structure of the tissue was gently disrupted by knocking cells into suspension with a pipette. If the tissue was provided in a pre-minced state in a flask, the above procedure was performed, but without the mincing step. In some conditions, the contents of the initial transport flask were spun down, if necessary. If any cells had adhered to the initial transfer flask, this flask was retained with fresh medium. This initial seeding of all of these flasks is referred to as passage 0.

After the viable cells had time to adhere to the flasks and begin growing (e.g., between 2 days and a week), at least one flask per culture medium condition was frozen down. During this process, about 30-50% of the medium in each of the flasks was changed every 2-3 days in a gentle manner to disturb the flasks as little as possible.

After the cells started actively growing, passage 1 was created by detaching the cells from the flasks using Accutase® cell detachment solution. Thereafter, the entire population of detached cells was moved to a new Primaria flask. This procedure breaks up the cell clumps that may form and allows the cells to better cover the surface area of the new flask.

After the cells were growing more evenly distributed across the flask, an evaluation was conducted to determine whether each flask was confluent to a sufficient degree to be expanded or if only a media change is necessary. In particular, if the flask was less than 75% confluent, the medium was changed. However, if the flask was more than about 75% confluent, one flask per medium condition was frozen according to known protocols, which left 1 or 2 flasks per condition remaining for passaging. These remaining flasks were expanded, which created Passage 2.

In order to create Passage 2, it was generally preferred to passage T-25 flasks into 10 cm cell culture dishes, rather than T-75 flasks because the lesser surface area of the 10 cm dishes ($55\ cm^2$) compared to the T-75 flask ($75\ cm^2$) is better for cell health and propagation. For example, expanding a T-25 flask into a 10 cm dish is roughly the equivalent of splitting the cells 1:2, whereas expanding the a T-25 flask into a T-75 flask is roughly the equivalent of splitting the cells 1:3, which can be bad for cell health. If the tumor cells had a difficult time attaching to the 10 cm dishes, Primaria was used to ease cell attachment.

Cells that were not ready for passage and the creation of Passage 2 (i.e., those that only had their media changed), were also re-evaluated and passaged as described above to create further Passage 2 cultures. At the time of creation of Passage 2, if there was still an original flask remaining with cells, the process for the creation of Passage 2 was performed on these flasks.

In general, the media in the Passage 2 dishes was changed on a Monday, Wednesday, and Friday schedule and the cultures were not expanded until the confluence reached 85-90%. Upon passaging to create Passage 3, the cells were split at a ratio of about 1:2, with one half of the cells passage to a T-75 flask and about one half being frozen. After the creation of Passage 3, cells were routinely cultured in T-75 flasks and the various media were evaluated as to relative effectiveness. Every two to three passages, the cells were split into multiple flasks so that one flask could be frozen down into two or three cryovials. Moreover, the cells that more rapidly grew in the flasks were frozen into greater numbers of cryovials (i.e., at a lesser concentration) compared to slower growing cells.

Media Formulations

Advanced DMEM/F12 was the basal medium used in addition to advanced RPMI. Most cells cultured did not display a preference for medium. The Advanced DMEM/F12 medium is a 1:1 mixture of Dulbecco's Modified Eagle Medium and Ham's F12 Medium, with the addition of ethanolamine, glutathione, ascorbic acid, insulin, transferring, AlbuMAX® I, lipid-rich bovine serum, and 1 mM sodium pyruvate. In addition, the following ingredients were added, 2.5% NuSerum IV, 1% 100× GlutaMax, 1% 100× Penicillin-Streptomycin, 10 ng/mL Cholera toxin, and 10 ng/mL Epidermal Growth Factor.

Sequencing

Genome Interrogation

For whole genome sequencing, one or both of the Illumina HiSeq2000 system and the Applied Biosystems' SOLiD system platform was used to fully interrogate the genomes of specimens. Sequencing allowed scientists to read the genome base pair by base pair and look for mutations that may cause disease.

Illumina HiSeq2000

The Illumina HiSeq2000 sequencing platforms enable scientific discovery with a full spectrum of applications, ranging from whole genome and targeted re-sequencing, to gene regulation analysis, SNP discovery and structural variation analysis, cytogenic analysis, DNA-protein interaction analysis, small RNA discovery and analysis, linkage analysis, FFPE sample analysis, expression analysis, genotyping, and sequencing-based transcriptome or methylation analysis.

Using Illumina's reversible terminator-based sequencing by synthesis chemistry, the HiSeq2000 delivers up to 200 GB of high quality data in fewer than 2 weeks, which is currently the industry's highest sequencing output and the fastest generation rate. This platform provides the investigator with previously unmatched cost savings and turn-around time for performing a wide variety of in-house experiments, including the ability to sequence two genomes to ~30× coverage in a single run.

Next-Generation Sequencing & Analysis

Next-generation sequencing is a genomic test that provides data on DNA mutations and alterations related to disease development. Next-generation sequencing allows TGen investigators to look at the entire genome or exome of a person. Four different types of DNA sequencing are currently used at TGen. Sanger sequencing is based on sequencing-by-synthesis and it uses a dye-termination electrophoretic approach. Illumina is another method based on sequencing-by-synthesis, but it uses a reversible dye-terminator approach. The ABI SOLiD system in the third system utilized by TGen. The SOLiD system is by Applied Biosystems and uses a synthesis by ligation system.

Data Analysis

Analysis and annotation involves error-free storing, transferring, backing-up, and processing of terabytes of data—validated processes for analysis were critical. Existing data processing and analysis pipeline are the result of managing internally generated data, and as one of the major participants in the International 1,000 Genomes Project (1 KG).

Next-Gen Data Processing Infrastructure

Researchers' current infrastructure is equipped to handle complete analysis of up to 1 Terabase of sequence data per month. The pipeline contains: (1) Massive storage infrastructures featuring expandable Isilon technology; (2) Massive cluster computing capabilities (30.1 Teraflops) with one of the 2 largest infrastructures dedicated to biomedical computing; (3) High memory computing with a 576 Gb shared memory machine; and (4) and next-generation file transfer with *Aspera*, with speeds reaching 100 Mb to most T1-capable institutes.

Next-Gen Data Processing and Analysis Pipeline

The Next-Generation Data Processing and Analysis Pipeline utilize validated software tools and produces standard platform-independent formats. Each software tool, including those internally developed, has been validated on multiple simulated and model data sets to characterize each tool's strengths and biases. At each step within the pipeline, statistics files are created to insure that all processes have completed and files are uncorrupted. Statistics files contain for example 'aligned bases', 'mismatch rate', and 'md5sums'. Early within a pipeline, several additional checks are invoked including estimates of overall coverage on a library, evenness on a library, quality of bases, and contamination checks.

Statistical Design

Bioinformatic techniques were used to determine candidate gene changes to assist in strategic planning for development of custom-designed inhibitory molecules or antibodies suitable for future therapeutic intervention. Unsupervised clustering techniques for expression profiling (i.e. k-means and hierarchical dendrograms) were used to identify clusters or sub-groups within the samples followed by an investigation of available clinical data to determine the biological source driving the sample segregation. Using identified biological segregators to bin samples, supervised techniques were implemented to find genes whose expression profiles could be used as potential markers.

Data Compilation

For each patient, investigators compiled a list of somatic alterations including: (i) somatic coding point mutations and frameshift mutations; (ii) note mutations in important domains or motifs (kinase, ligand binding, etc.); (iii) genes mapping within focal high level amplicons or homozygous deletions; (iv) genes involved in translocations/fusions; (v) rank order of expressed genes; (vi) germline mutations or SNPs involved in drug metabolism; and (vii) a list of potential targets for which drugs are available. Investigators also included genes that become evident only from integrated analysis of genome and transcriptome analysis, such as a gene mapping to a large hemizygous deletion region and contains an obviously inactivating frameshift or nonsense mutation in the retained allele.

Patient specific gene state data and processed information was assembled into a relational Gene Centric Characterization Database (GCCD). The GCCD integrated the disparate gene state annotation data and compiled all available genomic information to facilitate the efficient and effective access for knowledge mining of the various dimensions of gene states.

Knowledge and Medical Intelligence Mining

Profiling Input

The output of the whole cancer genome profiling for each of the patients on the study produced complex data, which was processed and analyzed by the bioinformatics team. This was assembled into the GCCD, which provided a comprehensive characterization of gene states and cataloguing of aberrant genes for each patient's cancer genome. The GCCD provided an organized compilation of molecular information (listed above) for subsequent knowledge mining, which involved a combination of expert and computationally assisted knowledge mining and interpretation to extract meaningful and clinically useful insights that can support the oncologist to select a therapy that is tailored to the patient's specific genomic context.

Knowledge Mining Approach

The innovative approach to 'Knowledge Mining and Translational Intelligence' leverages a multidisciplinary systems approach to modeling complex molecular process relationships. The general approach leverages modern process control systems, engineering principles, and hierarchical data representation strategies to achieve a top down abstraction of higher level concepts to more effectively reveal insights into novel drug targets and control points to more accurately predict vulnerabilities and drug response. The team has assembled commercially available tools and data resources, as well as public domain resources and custom algorithms and databases to link specific information from a single genome to knowledge in a way that supports 'mechanistic understanding' and 'biological interpretation' sufficient to be able to match and prioritize therapeutics based on the state of genes across the genome.

Translational Reporting

A knowledge mining analysis and translational report was generated for each patient. Each report provides an interpretation of the aberration list, a mechanistic explanation to describe the contextual vulnerabilities that were found.

RESULTS

Example 1—Creation of Patient-Derived Xenograft ("PDX") and Cell Line from Tumor Samples Initially, tumor cells isolated from a CNS metastasis (the spine) in a patient with a primary tumor in the lungs were used to establish in vivo and in vitro models. Referring to FIG. 2A, introduction of these metastasized tumor cells into the flank of NSG mice produces a viable tumor that shows an increase in tumor weight over the course of a forty-week experiment. Similarly, as shown in FIG. 2B, by employing the methods described above, a cell line was created using the same metastasized tumor cells.

Figure 3:
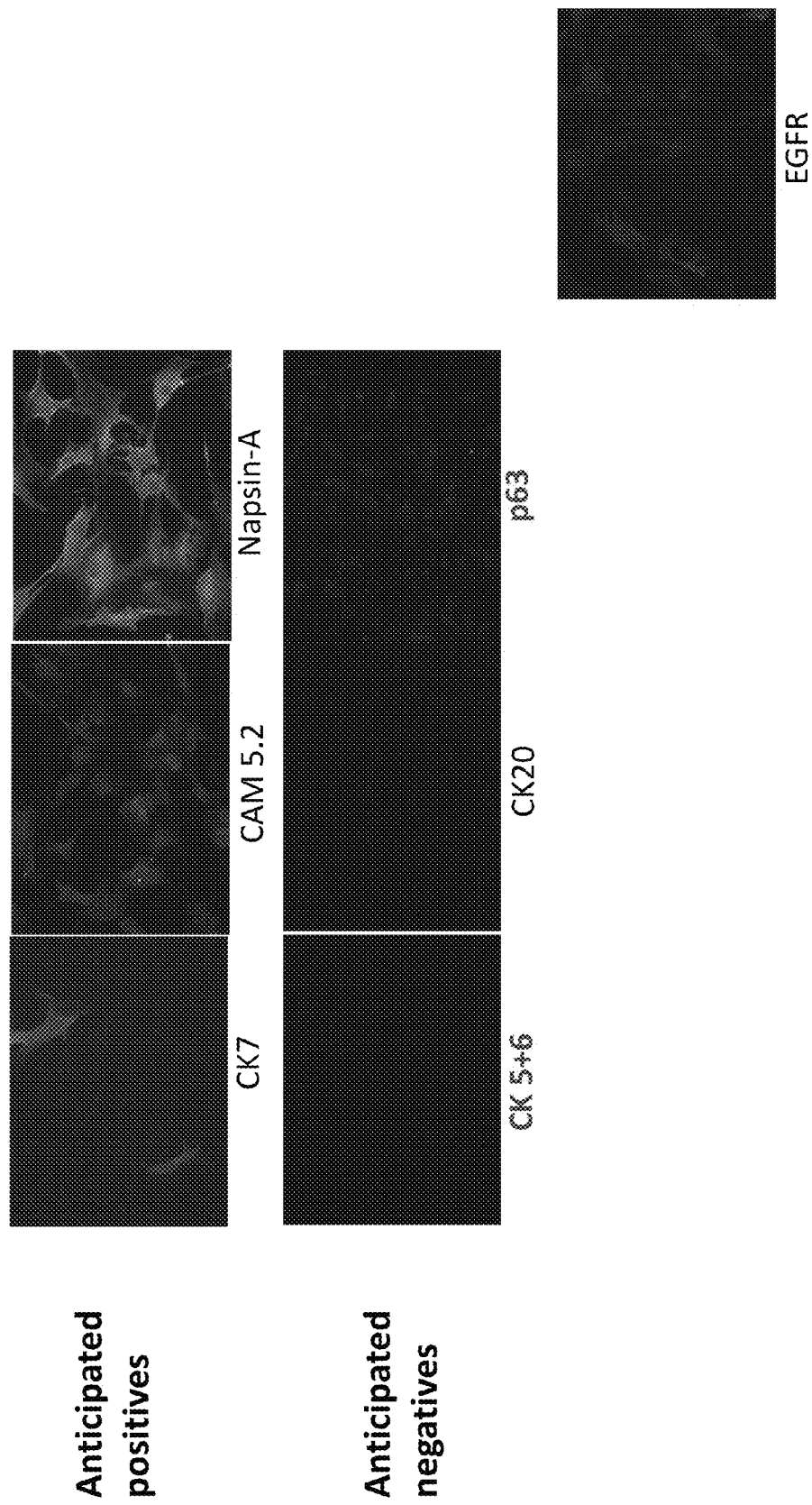
FIG. 3 is a series of images where a cell line created from a patient-derived metastatic tumor was stained using immunofluorescence techniques to assess the expression of a series of pathological phenotype markers.

Example 2—Confirmation of Pathological Phenotypes of Patient Cancers in In Vitro Cell Lines Referring now to FIGS. 3-6, confirmation of pathological phenotypes was seen in the cells lines created from the CNS metastases from multiple patients. First, a cell line was created from the spine metastasis of a patient with adenocarcinoma of the lungs. As illustrated in FIG. 3, after the $17^{th}$ passage, the cells were stained to assess marker expression to ensure that the pathological phenotype determined by a pathologist upon tumor resection was still detectable. In this case, the pathologist determined that the CNS metastasis at the time of resection was positive for markers CK7 and CAM 5.2. Staining of the cell line shows that the markers that were anticipated to stain positive and anticipated to stain negative (i.e., not present or not detectable) based on the pathologist's determination at the time of tumor resection were similar in the cell line. In addition, the cell line largely stained negative for EGFR.

Figure 4:
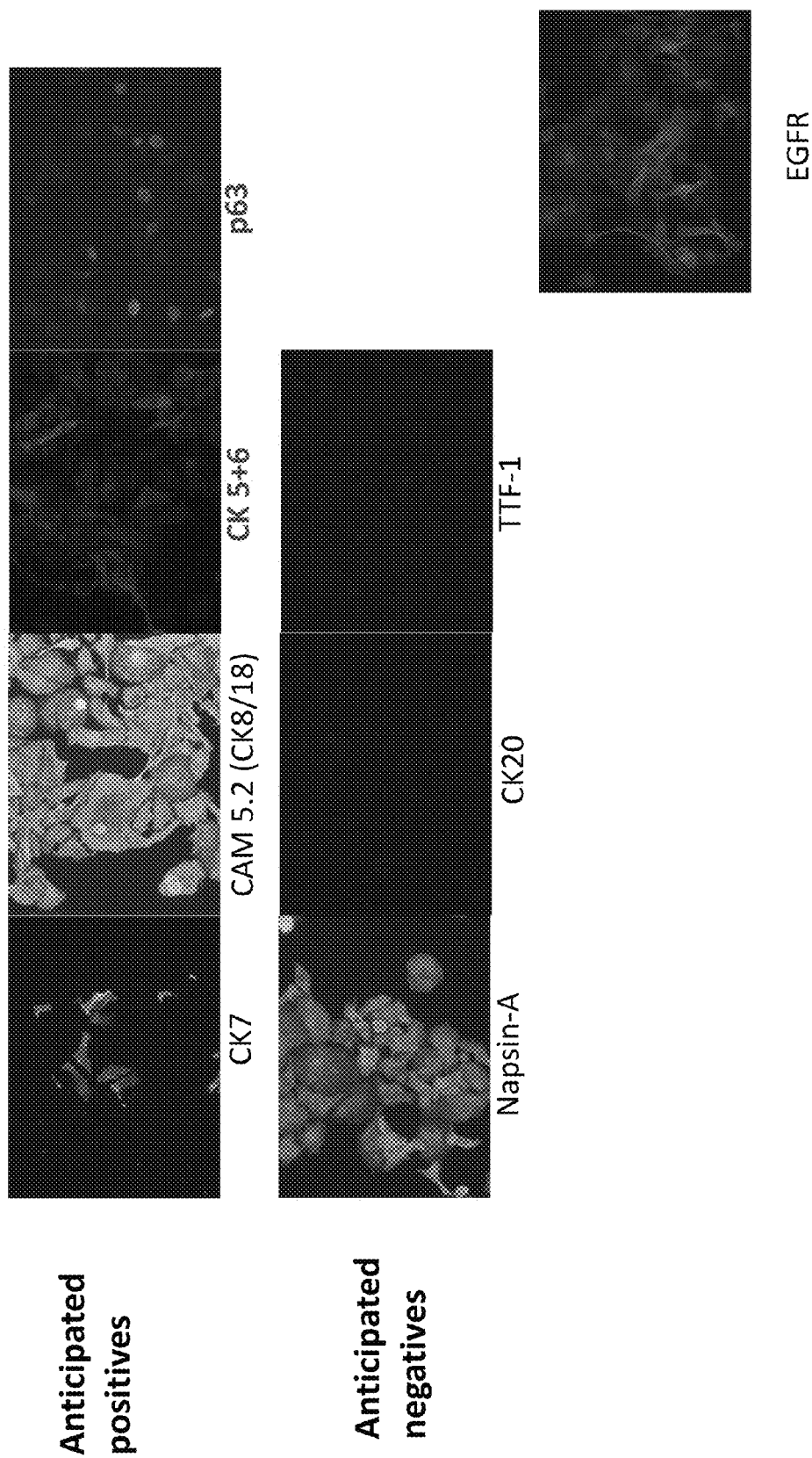
FIG. 4 is a series of images where a cell line created from a patient-derived metastatic tumor was stained using immunofluorescence techniques to assess the expression of a series of pathological phenotype markers.

Similarly, a cell line was created from the brain metastasis of patient with poorly differentiated squamous cell carcinoma of the lung. As illustrated in FIG. 4, after the fourth passage, the cells were stained to assess marker expression to ensure the pathological phenotype determined by a pathologist upon tumor resection was still detectable. In this case, the pathologist determined that the tumor cells from the metastasis were positive for CK7, CK5+6, and p63 and negative for CK20, Napsin-A, and TTF-1. The results of the staining of the cell line largely confirmed the pathologist's report. Although the cell line stained positive for Napsin-A, scientific literature suggests that these cells should actually stain positive for this marker. In addition, the cell line stained at least partially positive for EGFR.

Figure 5:
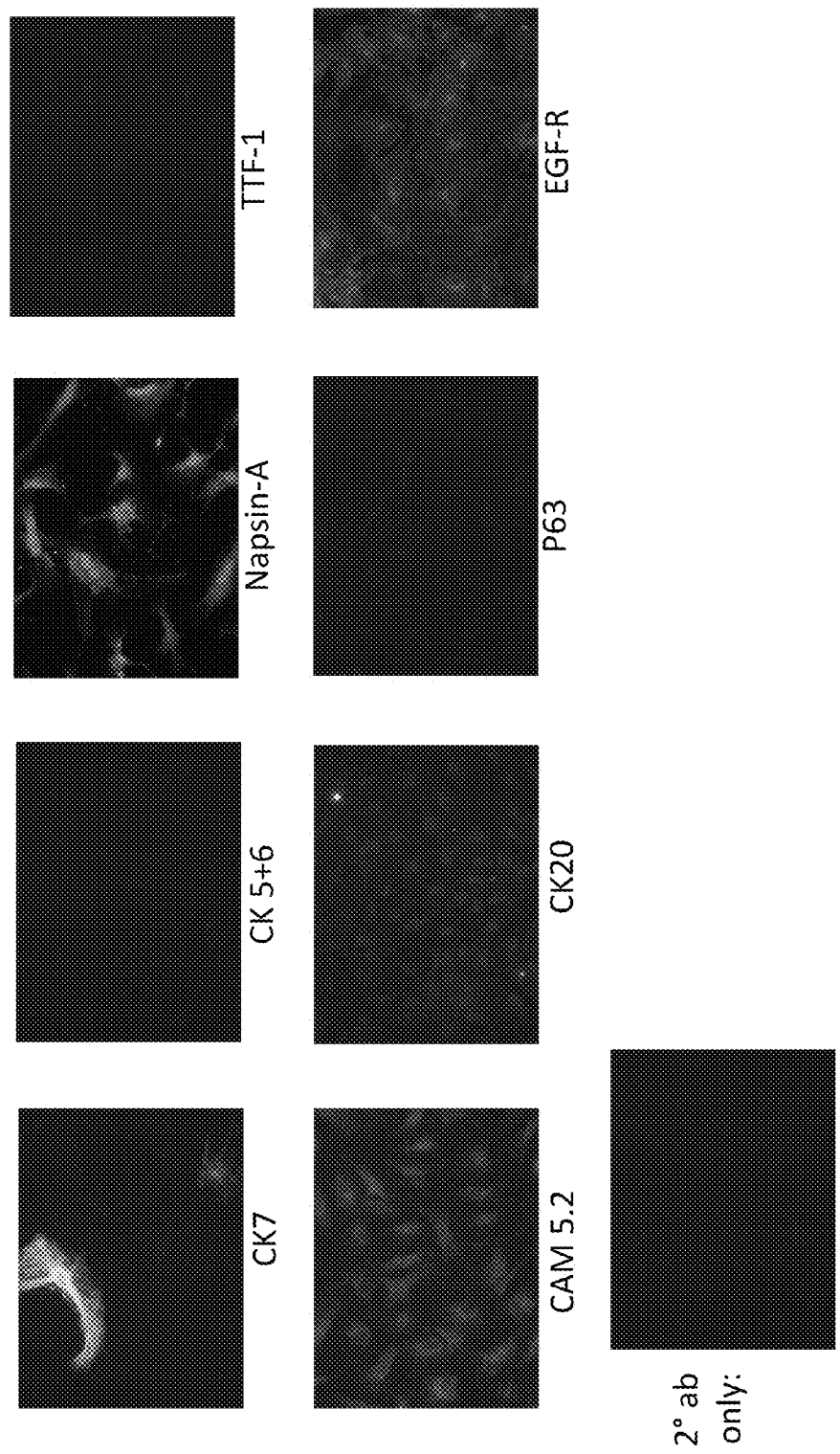
FIG. 5 is a series of images where a cell line created from a patient-derived metastatic tumor was stained using immunofluorescence techniques to assess the expression of a series of pathological phenotype markers.

Referring now to FIG. 5, a similar experiment was conducted on the sixth passage of a cell line created from the brain metastasis from a patient with carcinoma of the lung that exhibited features of poorly differentiated adenocarcinoma. In this case, the following markers were expected to stain positive for these cells: CK7, Napsin-A, TTF-1, CAM5.2, and EGFR and the following markers were expected to stain negative: CK5+6, CK20, and p63. The results in FIG. 5 largely confirm the expected results. One aberration is the staining of TTF-1, which was expected to be positive. However, other cells that also should have stained positive were found to not stain positive using this antibody. As such, there could be a problem with the antibody itself.

Figure 6:
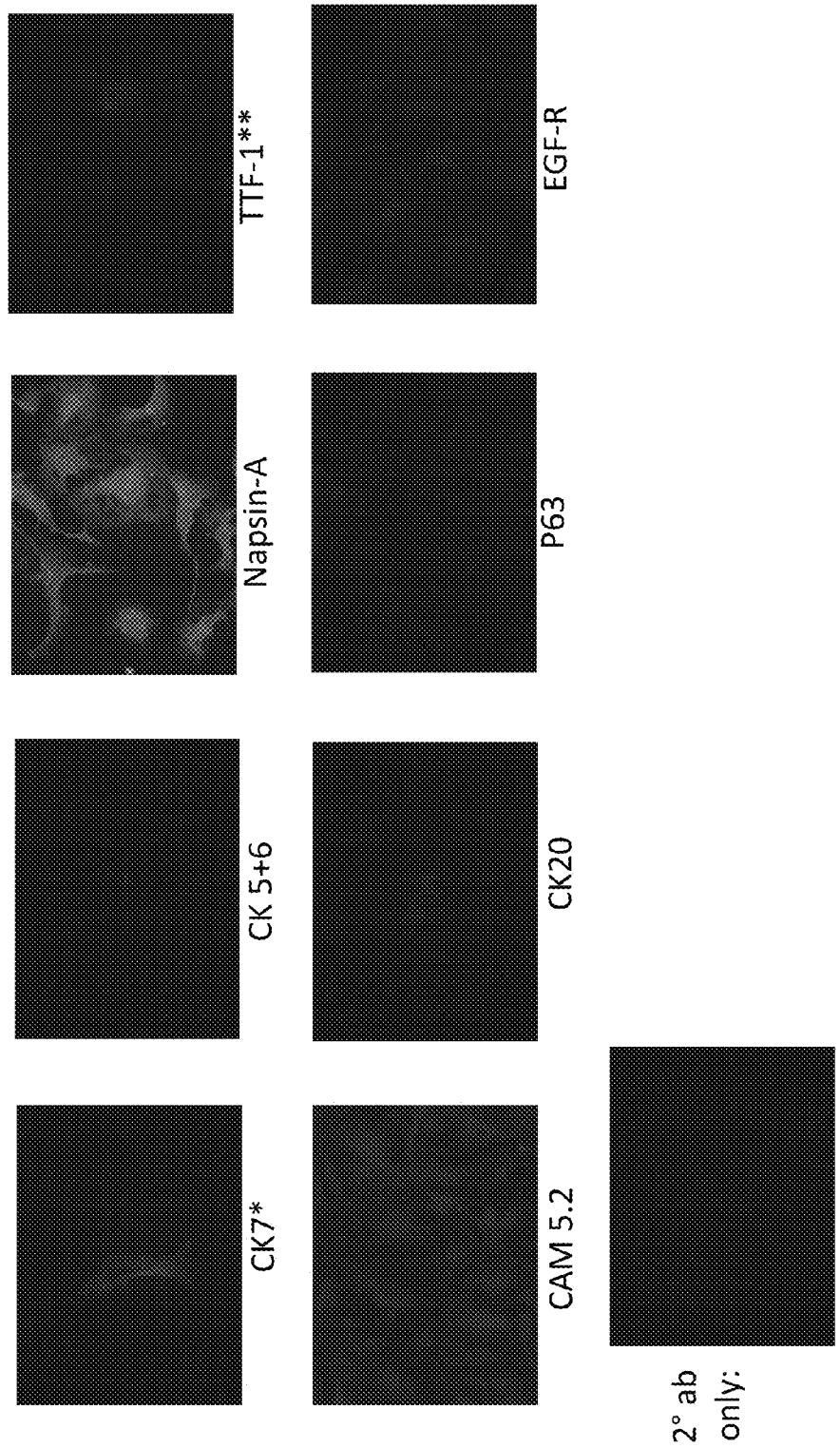
FIG. 6 is a series of images where a cell line created from a patient-derived metastatic tumor was stained using immunofluorescence techniques to assess the expression of a series of pathological phenotype markers.

Referring now to FIG. 6, a similar experiment was conducted on the seventh passage of a cell line created from the brain metastasis from a patient with poorly differentiated adenocarcinoma of the lung. In this case, the following markers were expected to stain positive for these cells: CK7, Napsin-A, TTF-1, CAM5.2, and EGFR and the following markers were expected to stain negative: CK5+6, CK20, and p63. The results in FIG. 6 largely confirm the expected results. One aberration is the staining of TTF-1, which was expected to be positive. However, other cells that also should have stained positive were found to not stain positive using this antibody. As such, there could be a problem with the antibody itself.

Example 3—Case Study Using Preclinical Model

In this case study, samples from a 70-year old white, non-Hispanic male were obtained. In particular, tumor samples from the primary tumor (lung adenocarcinoma) and from the CNS metastasis (spine) were used in the following experiments. In this study, the following techniques were employed to compare the molecular profile of the CNS tumor and normal, non-cancerous tissue from the same subject: exome sequencing, RNA sequencing, DNA methylation analysis, and reverse phase protein array.

The molecular profile of the CNS metastasis showed multiple changes. In particular, the molecular profile in the CNS metastasis showed a total of 33 mutations in the exome (i.e., RNA-encoding regions of the DNA) of the patient, with the following included as exemplary markers: KRAS, ABCB4, ABCG8, MAP3K1, TGFBR1, TP53, and VAV3. In addition, copy number variations were also detected in HDAC9, KRAS, FGFR2, JAK2, MDM2, VAV3, and WT1, among other markers of interest.

In view of these changes in the patient's molecular profile, a treatment model was created. Specifically, NSG mice that had previously received PDX from this patient, as illustrated in FIG. 2A, were treated with one or more pharmaceutical compositions to determine how the tumor cells of the PDX would respond to therapies selected based on the molecular profile. For example, in view of the G12C mutation in the KRAS gene and the additional amplification this same gene found in the subject's exome, a MEK inhibitor (i.e., a pharmaceutical that targets the mitogen-activated kinase kinase enzymes MEK1 and MEK2) was selected. In this experiment, the MEK inhibitor selected was PD0325901. In addition, the detection of the HDAC9 amplification drove the selection of a drug that has been previously shown efficacy of epigenetic therapy in metastatic lung cancer, suberanilohydroxamic acid or SAHA, which is a potent HDAC inhibitor. Moreover, both of these agents have been shown to be blood-brain barrier penetrant such that if this combination was administered to an individual with CNS metastasis, the pharmaceutical would be able to reach the location of the metastasis.

Figure 7:
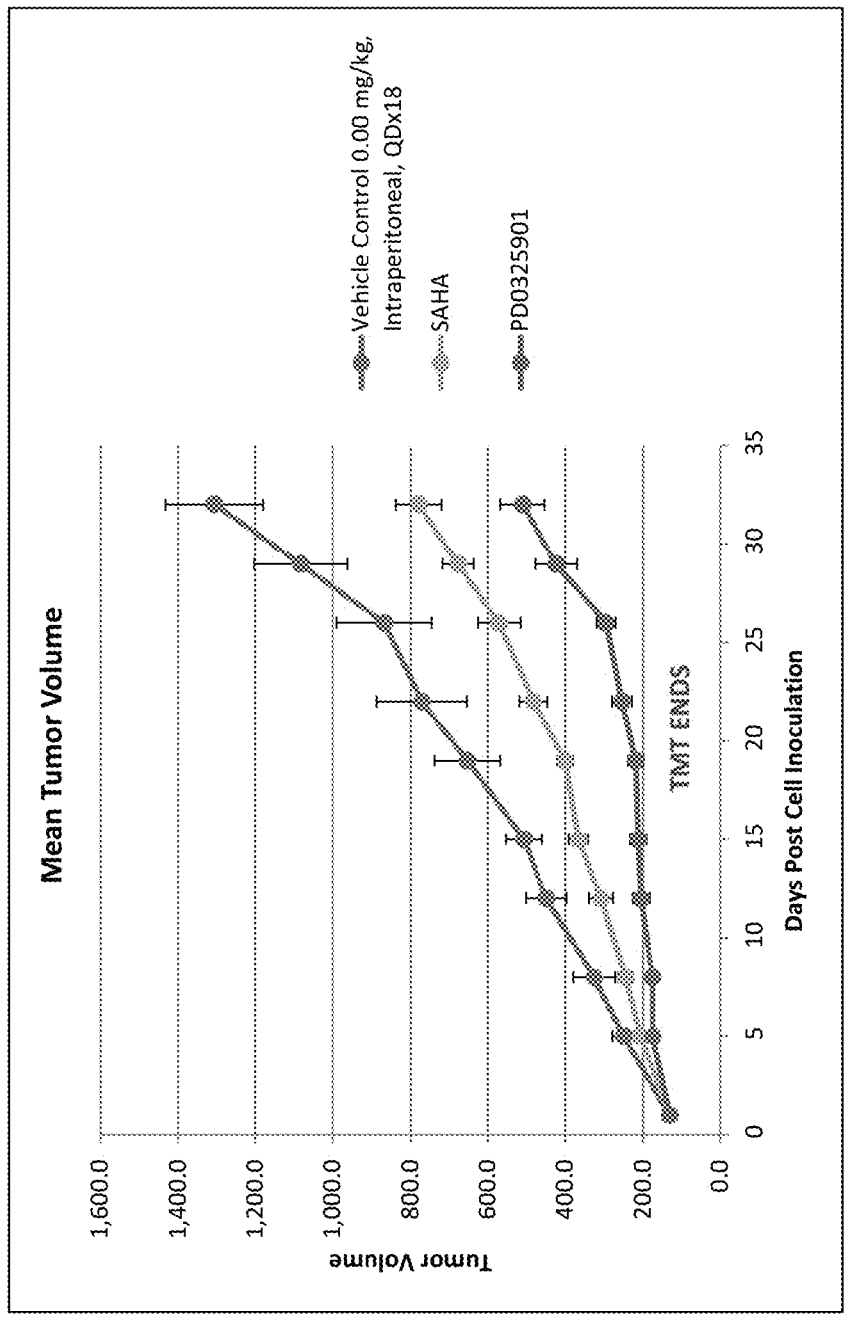
FIG. 7 is a graph representing the impact of various treatments on patient-derived xenograft from a metastatic tumor in NSG mice.

After establishing which treatments were to be used in the case study, 15 animals comprising the PDX were divided into three groups. A first group received vehicle only via intraperitoneal injection each day for 18 days. A second group received SAHA (100 mg/kg) via oral gavage each day for 18 days and a third group received PD0325901 (20 mg/kg) each day for 18 days via oral gavage. Both during and after treatment, tumor volume was measured in each of the mice and the data is plotted in FIG. 7. Specifically, the PDX animals that received the MEK inhibitor experienced little to no tumor growth during the treatment timeframe. Moreover, the PDX animals that received the HDAC inhibitor experienced reduced tumor growth compared to the vehicle control animals. In addition, after treatment stopped (day 18, as reflected by the arrow in FIG. 7), the rate of tumor growth in the animals that received the MEK inhibitor was reduced compared to animals in the SAHA and control groups. Given this data, it appears that the tumor growth in the CNS metastasis of this subject was largely driven by one or both of the KRAS mutation or amplification.

Figure 8:
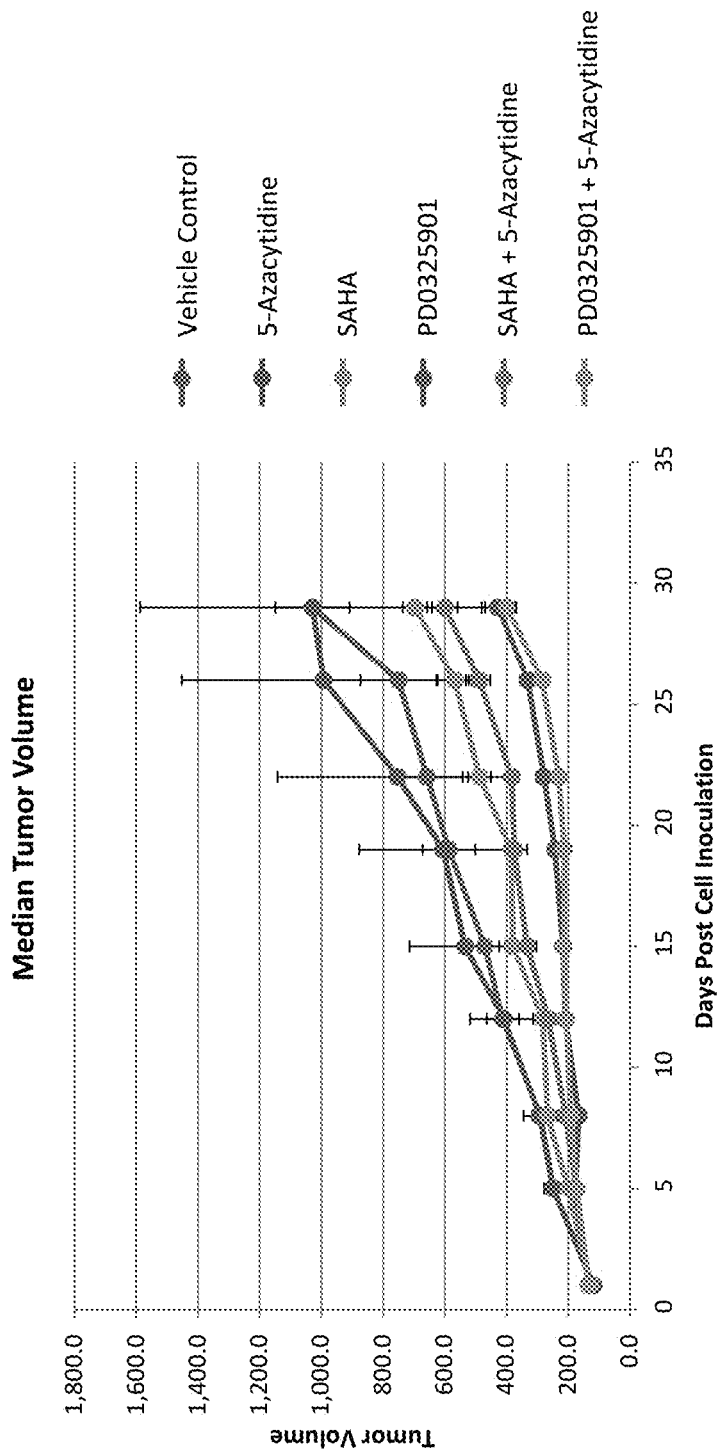
FIG. 8 is a graph representing the impact of various treatments on patient-derived xenograft from a metastatic tumor in NSG mice.

Additional experiments were conducted to investigate the potential impact of combination drugs. Referring now to FIG. 8, the drug treatment experiments described above were repeated with an additional pharmaceutical composition, 5-Azacytidine, which is a nucleoside analog that is an FDA-approved treatment for some forms of cancer. Each of the treatment conditions described above with respect to the PDX animals was repeated and 5-Azacytidine was administered at 2.0 mg/kg via intraperitoneal injection. In addition, combinations of 5-Azacytidine and either SAHA or PD0325901 were also used as treatment conditions. The results illustrate that although 5-Azacytidine by itself did not serve as an efficacious treatment for this tumor, the combinations of 5-Azacytidine with SAHA or PD0325901 appeared to provide enhanced treatment (i.e., slowed tumor volume growth) compared to SAHA and PD0325901 alone.

Example 4—Additional Experimentation

FIG. 9 illustrates the samples collected from various patients for which some aspects of the instant invention were employed in preparing and assessing preclinical model systems and methods. For example, the "origin" column reflects the type of cancer with which the patient in question was diagnosed (e.g., "NSCL" refers to non-small cell lung cancer, "SCLC" refers to small cell lung cancer, "breast" refers to breast cancer, and "colon" refers to colon cancer). Moreover, the data in this chart illustrates the different types of samples obtained from the various patients and the resulting aspects of the preclinical system developed with those samples. For these various patient samples, at least of the portion of the samples were subject to the following diagnostic/therapeutic-selection/molecular techniques: whole-genome sequencing to detect single nucleotide variations, insertion/deletions, copy number variations, RNA sequencing, DNA methylation analyses, phospho-proteomics, and drug-sensitivity experiments (i.e., using patient-derived xenografts).

Figure 10A:
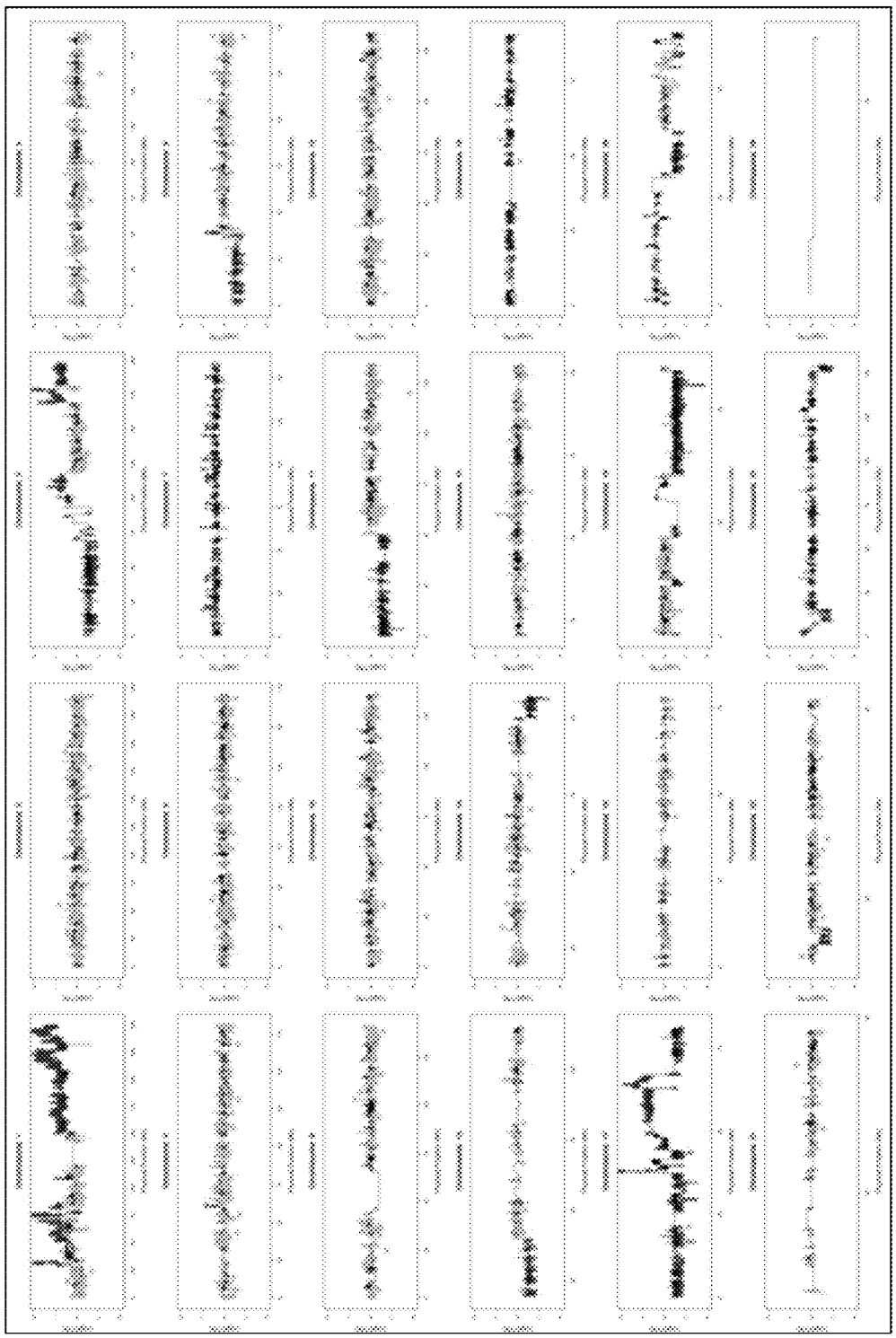
FIGS. 10A, 10B, 10C, and 10D are a series of copy number variation plots illustrating the overlapping genomic information provided by samples obtained from a patient and samples from the patient that have been processed.
Figure 10B:
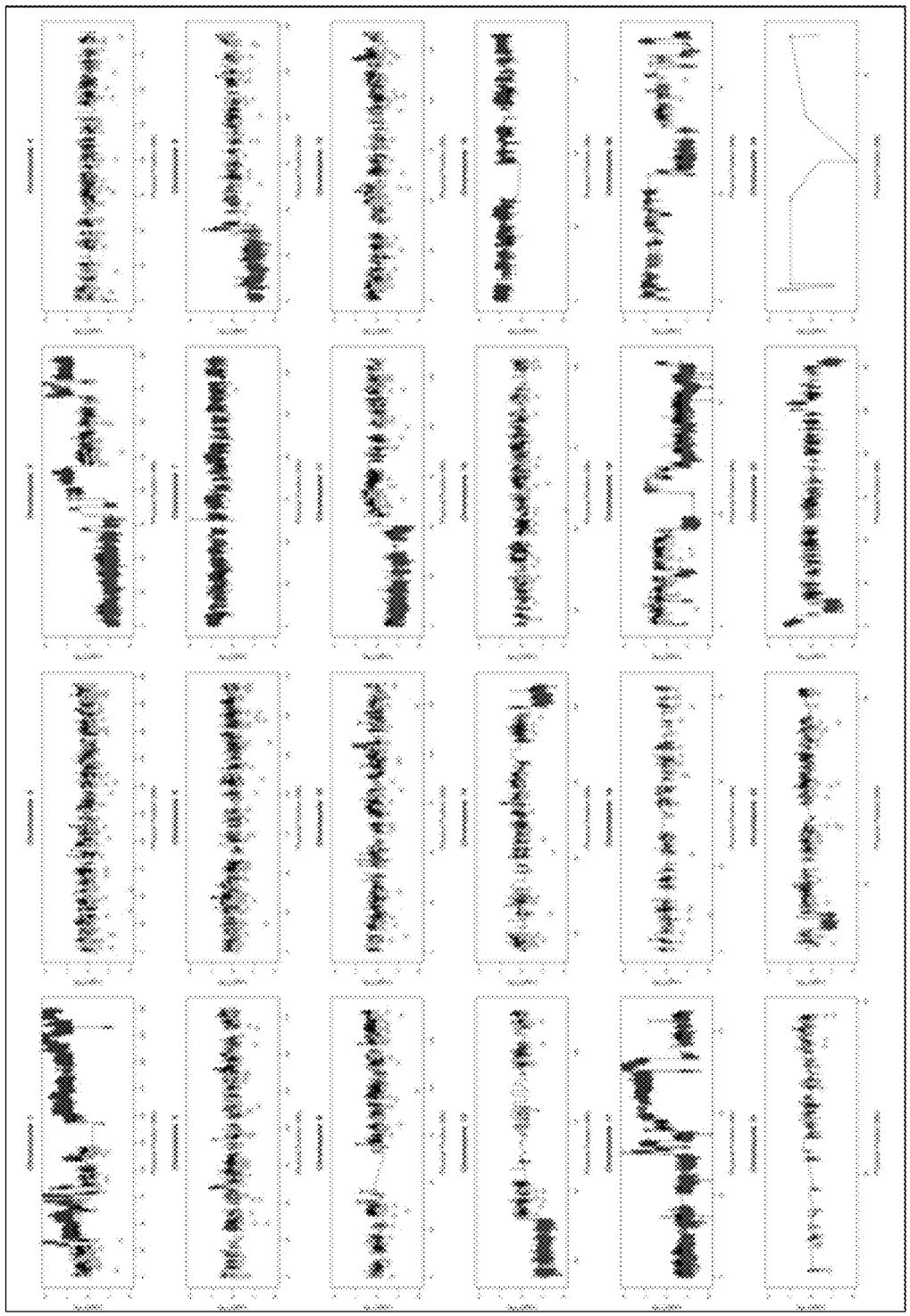
Figure 10C:
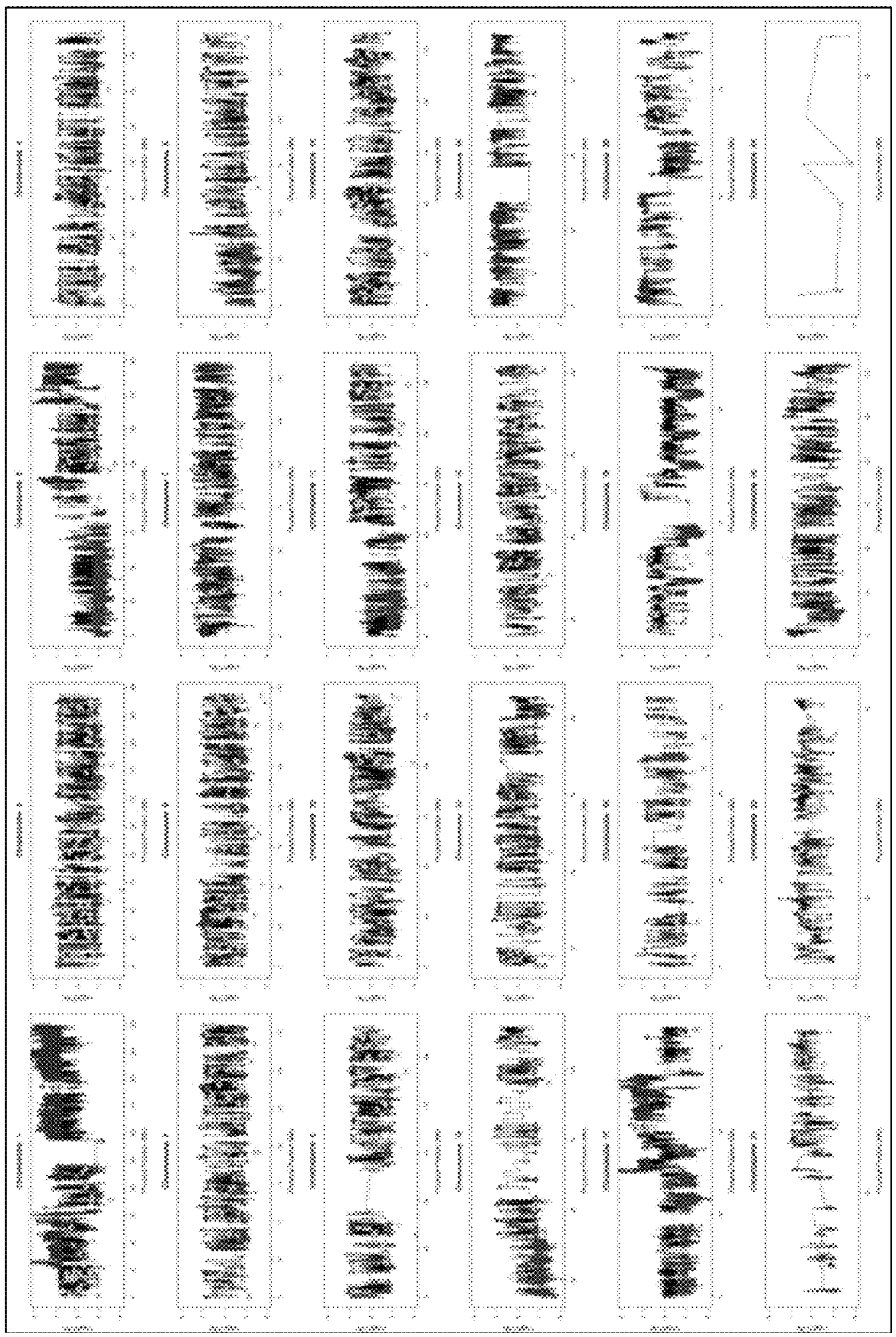
Figure 10D:
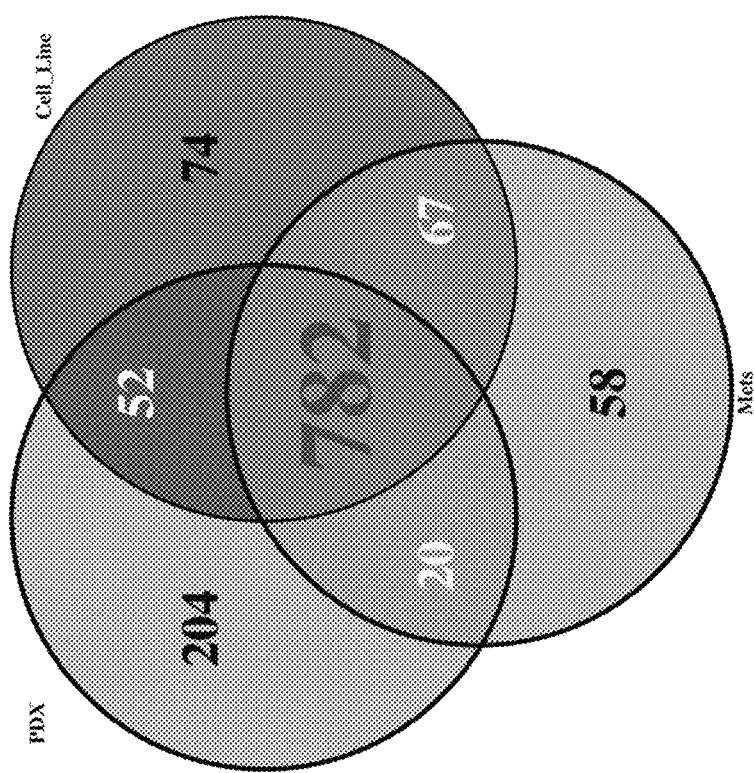

FIGS. 10A, 10B, 10C, and 10D illustrate the overlapping diagnostic capabilities achieved by obtaining multiple samples from a patient. FIGS. 10A-10C are copy number variation plots obtained from various samples and processed materials obtained from a single patient with Her2+ breast cancer that had metastasized to the central nervous system (e.g., at least the brain of the patient). In these figures, it can be seen that the pattern of copy number variation is generally uniform in the analyses of the patient metastatic tumor (FIG. 10A), the patient-derived xenograft (FIG. 10B), and the cell line that was created using the patient's tumor-derived cells (FIG. 10C), which further supports the clinical utility of the systems and methods of this invention. Moreover, the Venn diagram in FIG. 10D further illustrates the overlap in copy number variation common to all of the above samples.

Figure 11:
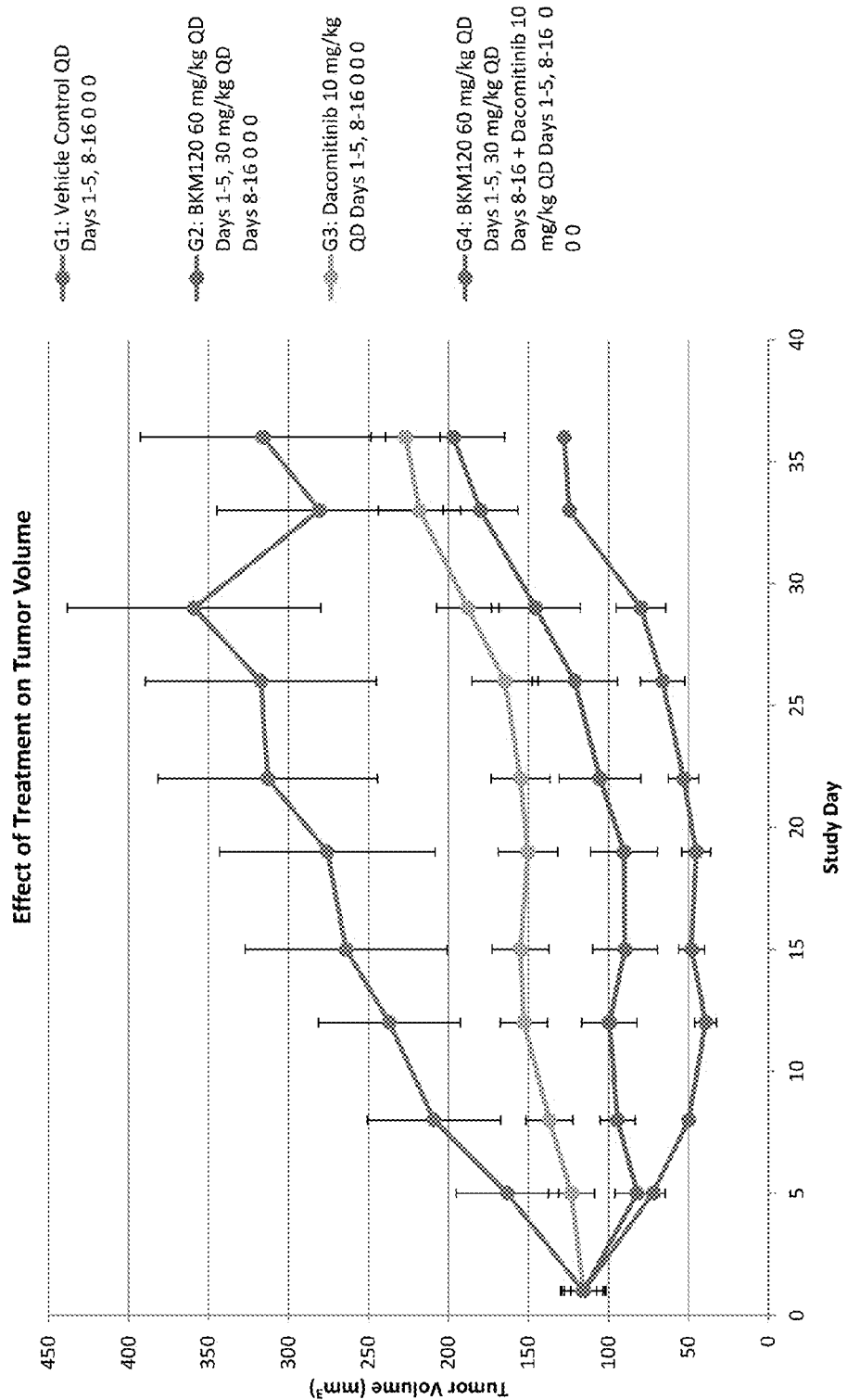
FIG. 11 is a graph representing the impact of various treatments on patient-derived xenograft from a metastatic tumor in mice.

FIG. 11 further illustrates the effect of various treatments on tumor volume in patient-derived xenograft models from the patient's samples reflected in FIGS. 10A-10D. Specifically, the results of the molecular analyses (e.g., whole-genome sequencing, RNA sequencing, exome sequencing, DNA methylation analysis, etc.) revealed that inhibition of ERBB2 and PI3 kinase could potentially provide an efficacious therapeutic strategy for the patient. Thereafter, tumor volume was measured for the various drug combinations detailed in FIG. 11. In particular, the treatments of BKM120 (PI3 kinase inhibitor) and dacomitinib (ERBB2 inhibitor) provided the most efficacious treatment of the various treatment conditions.

Figure 12:
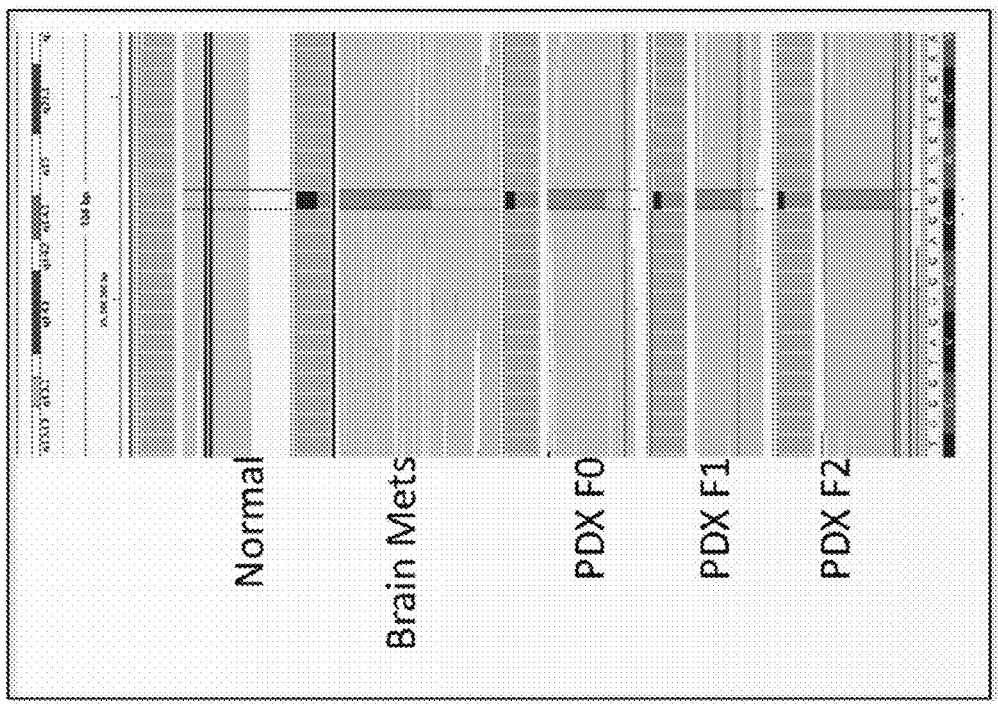
FIG. 12 is a sequence alignment illustrating a mutation in the patient's KRAS gene in a normal non-cancerous sample, a sample of the patient's tumor, and patient-derived xenografts originating from the patient's tumor. This figure also includes a list of mutations and copy number variations detected in the patient's genome.
Figure 13:
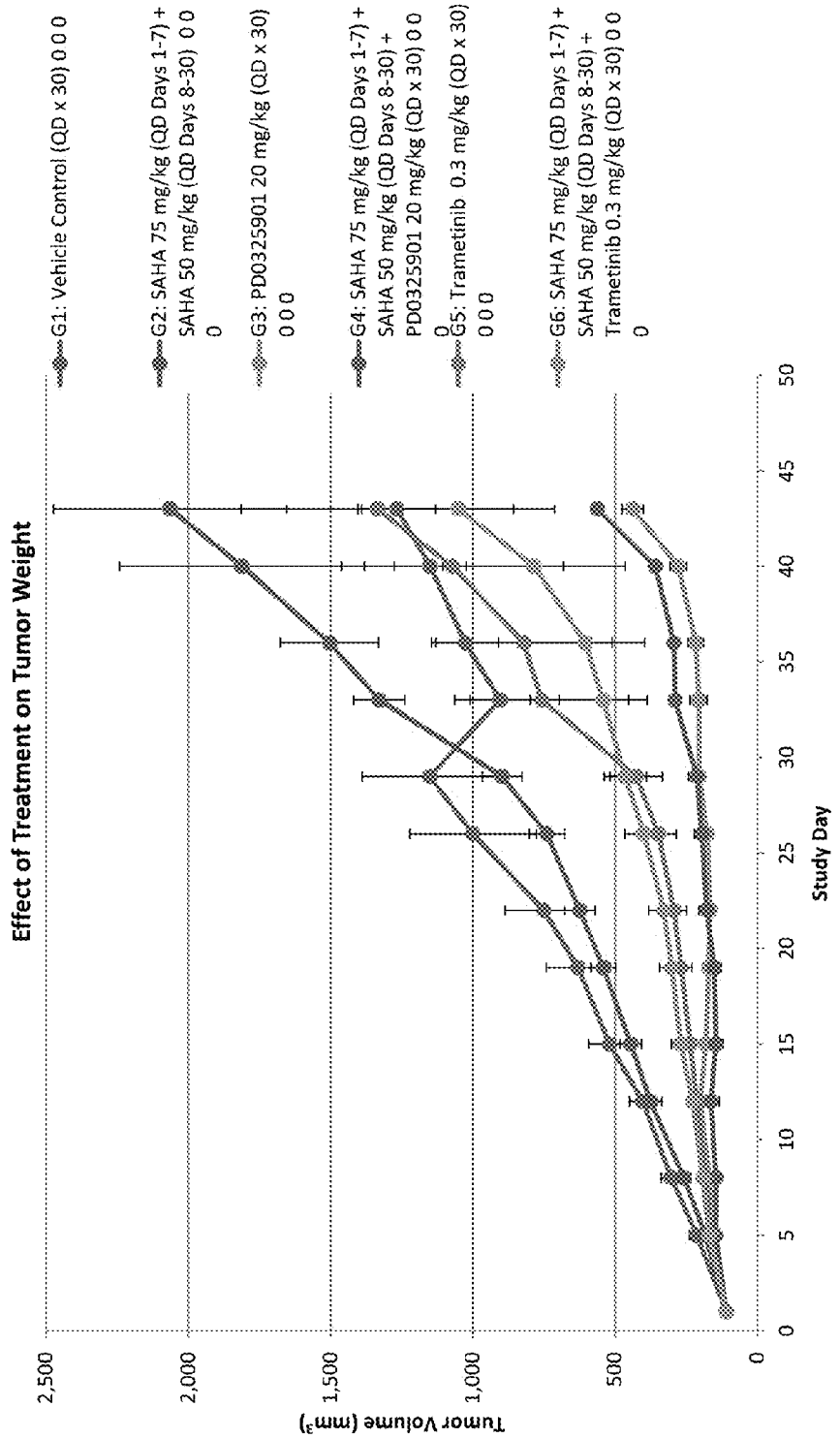
FIG. 13 is a graph representing the impact of various treatments on patient-derived xenograft from a metastatic tumor in mice.
Figure 14:
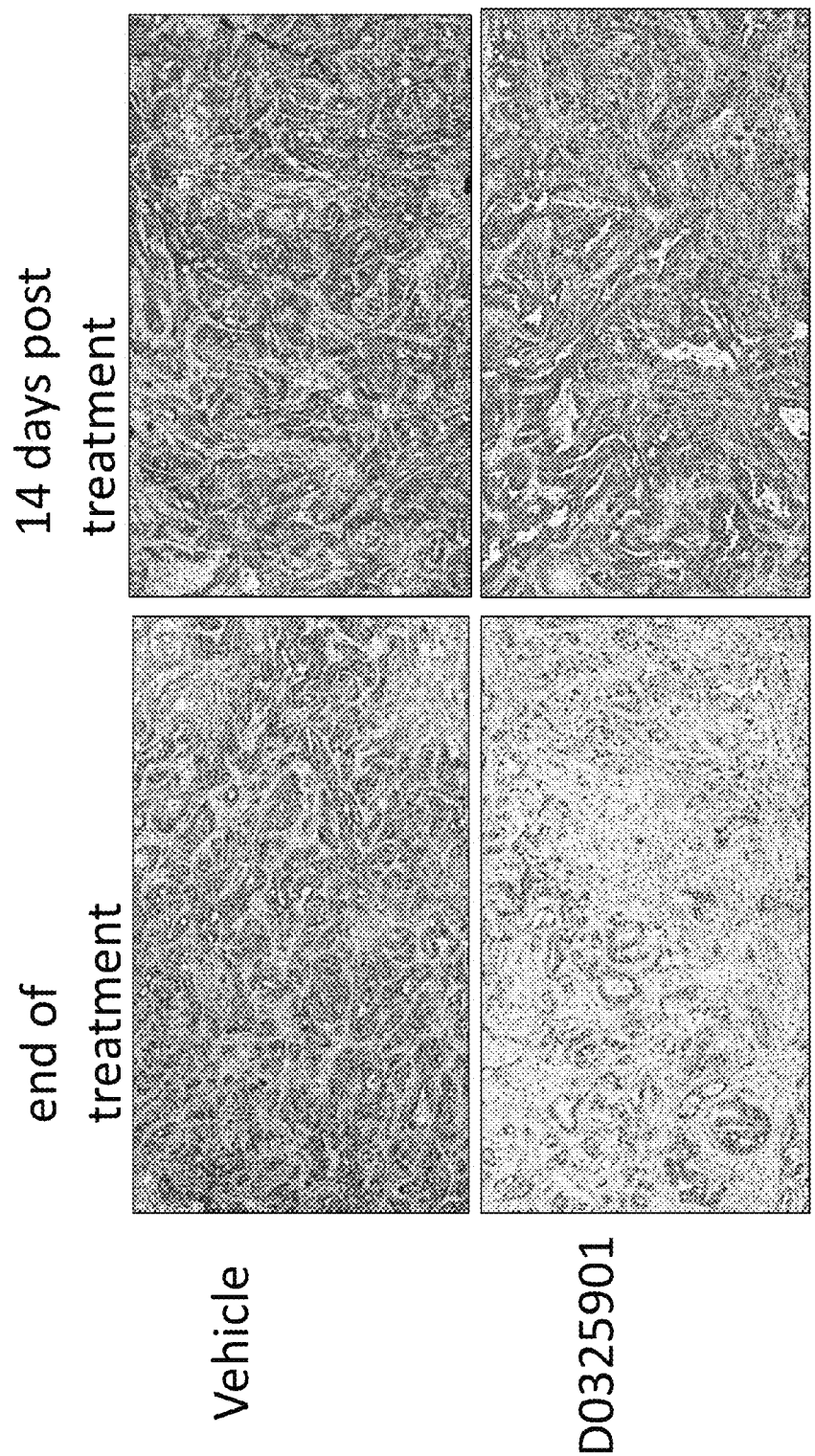
FIG. 14 is an immunohistochemistry study of tissue from the patient whose samples were detailed in FIGS. 12 and 13. In this study, an anti-phosphorylated ERK antibody was used to assess ERK phosphorylation in the various treatment conditions.

Referring next to FIGS. 12 and 13, samples from a different patient (i.e., a patient with lung cancer that metastasized to portions the central nervous system) that were analyzed using some aspects of the instant invention. For example, as illustrated in FIG. 12, molecular analyses (e.g., whole-genome sequencing, RNA sequencing, exome sequencing, DNA methylation analysis, etc.) revealed multiple important mutations (e.g., KRAS, ABCB4, MAP3K1, TFGBR1, TP53, and VAV3) and copy number variations (e.g., HDAC9, KRAS, FGFR2, JAK2, MDM2, and VAV3). Moreover, the discovery of the KRAS mutation was observed in tumor-derived samples from the patient (e.g., PDX) compared to normal, non-cancerous samples obtained from the patient. As a result of this analysis, it was determined that a MEK inhibitor (e.g., PD0325901) should be employed in the patient-derived xenograft context to assess potential for therapeutic efficacy. As illustrated in FIG. 13, the treatment conditions in which a MEK inhibitor was used displayed the most reduced gains in tumor weight, which suggests a therapeutic benefit. Finally, referring to FIG. 14, the use of the MEK inhibitor also reduced ERK phosphorylation in the metastasis cells during treatment compared to vehicle alone. Moreover, 14 days after treatment with the MEK inhibitor, ERK phosphorylation returned to vehicle-treatment levels.

Figure 15A:
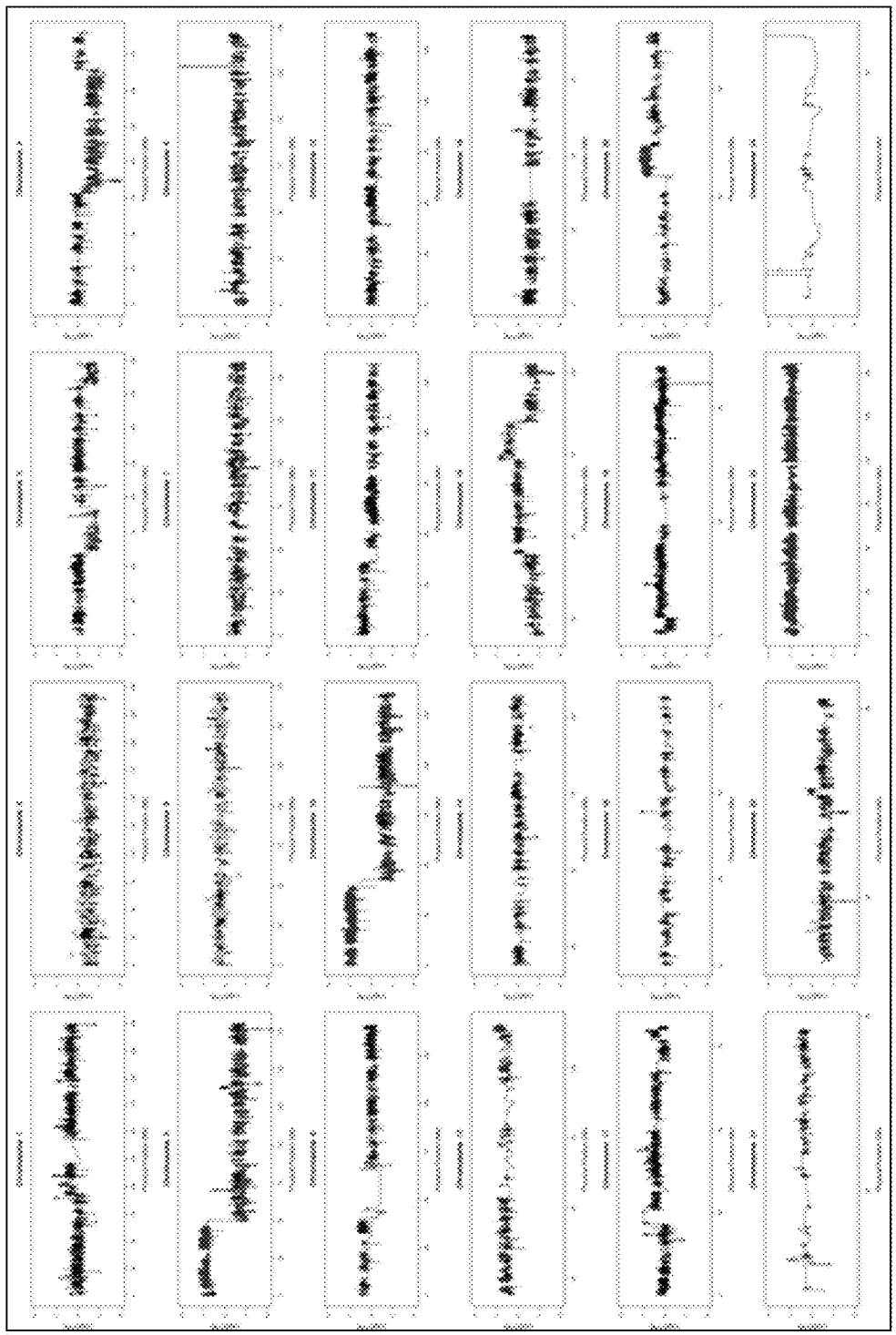
FIGS. 15A, 15B, and 15C are a series of copy number variation plots illustrating the overlapping genomic information provided by samples obtained from a patient and samples from the patient that have been processed.
Figure 15B:
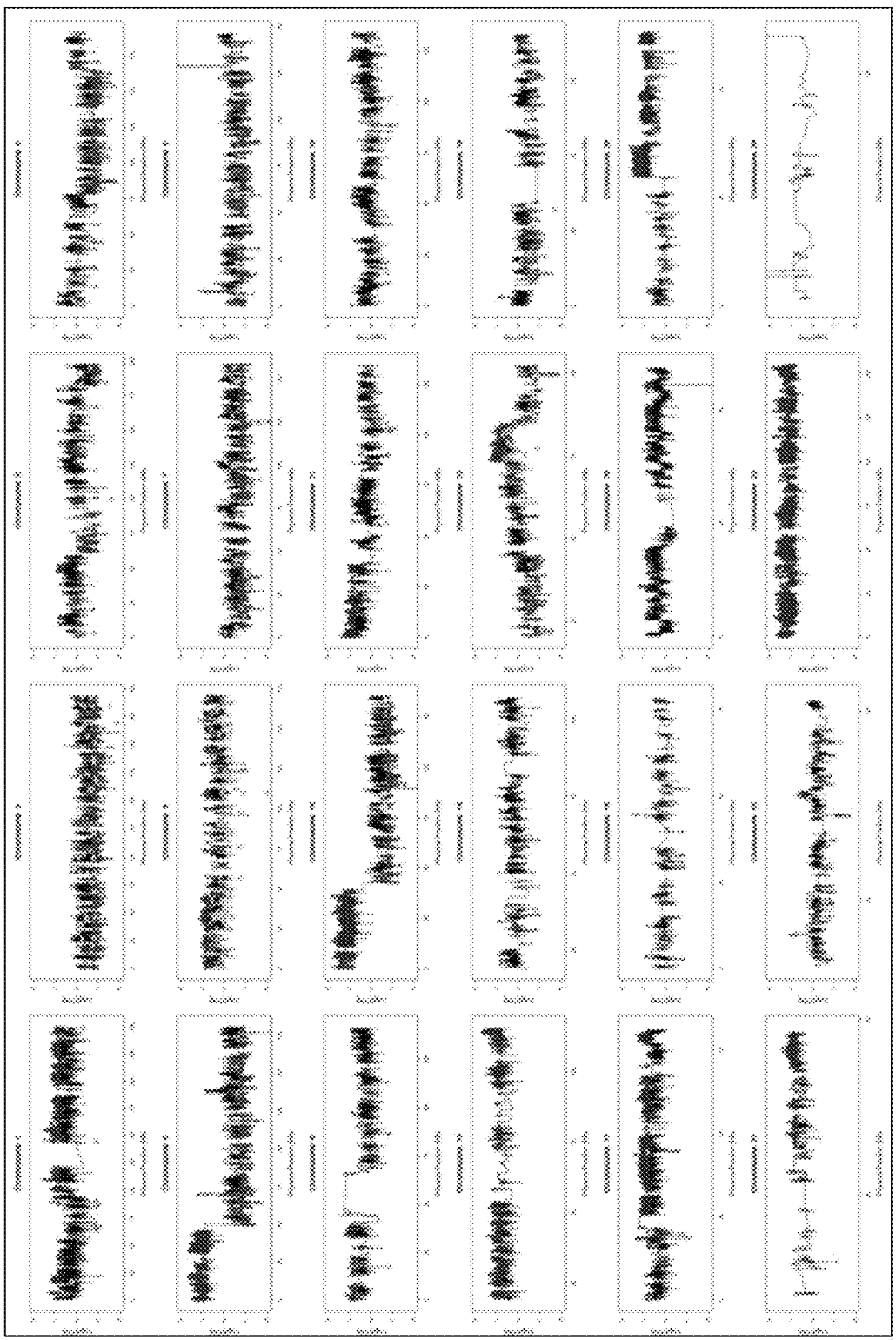
Figure 15C:
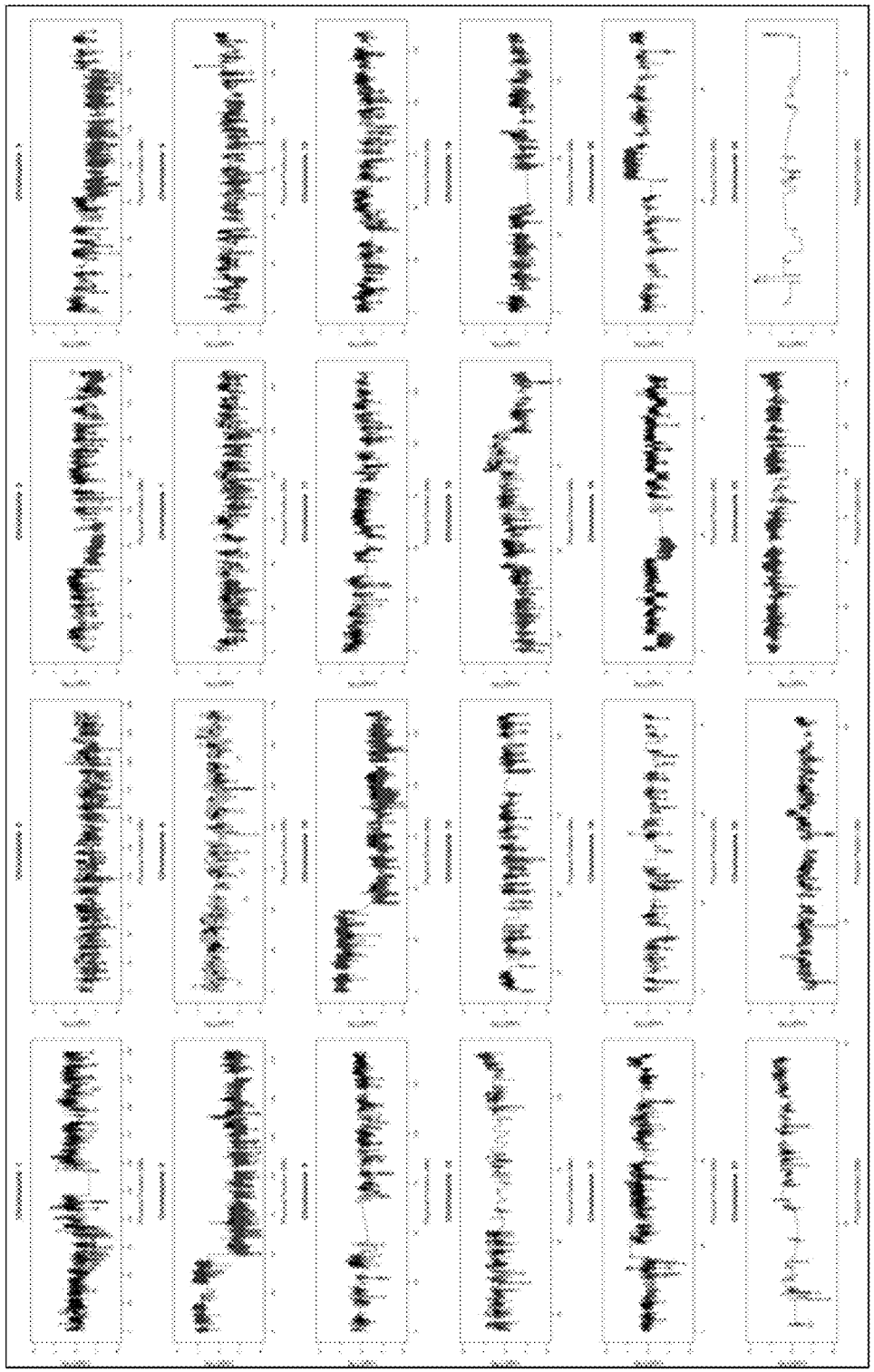

FIGS. 15A, 15B, and 15C, further illustrate the overlapping diagnostic capabilities achieved by obtaining multiple samples from a patient. FIGS. 15A-15C are copy number variation plots obtained from various samples and processed materials obtained from a single patient with small cell lung carcinoma that had metastasized to the central nervous system (e.g., at least the brain of the patient). In these figures, it can be seen that the pattern of copy number variation is generally uniform in the analyses of the patient metastatic tumor (FIG. 15A), the patient-derived xenograft (FIG. 15B), and the cell line that was created using the patient's tumor-derived cells (FIG. 15C), which further supports the clinical utility of the systems and methods of this invention.

Figure 16:
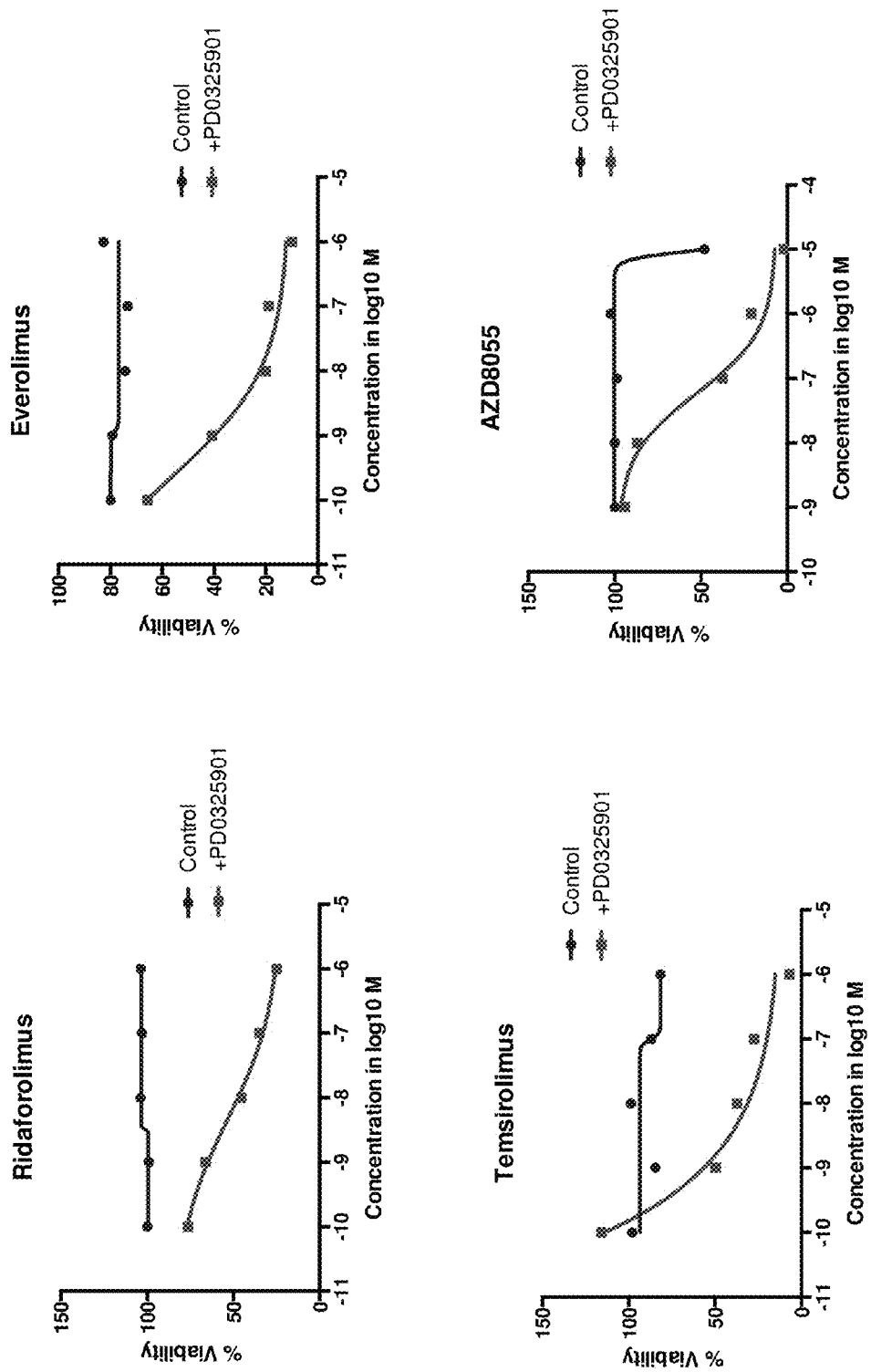
FIG. 16 is a series of rapalog-based treatment regimens based on the selection of mTOR as a potential therapeutic target for the patient whose samples were used in FIG. 15. Rapamycin-based derivatives (ridaforolimus, everolimus, temsirolimus, and AZD8055) were tested alone and in combination with PD0325901, a MEK inhibitor, to assess viability of tumor cells derived from the patient.
Figure 17:
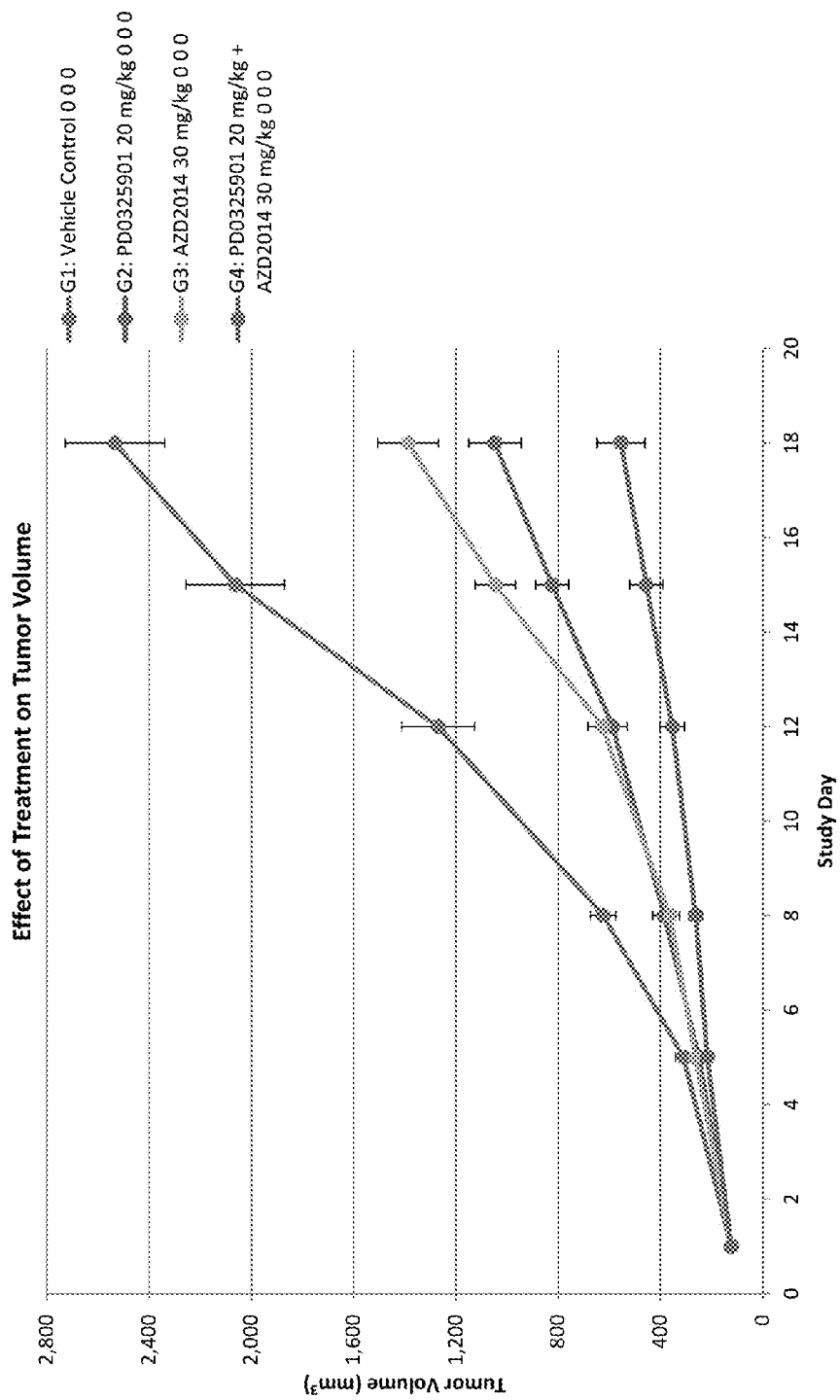
FIG. 17 is a graph representing the impact of various treatments on patient-derived xenograft from a metastatic tumor in mice.
Figure 18:
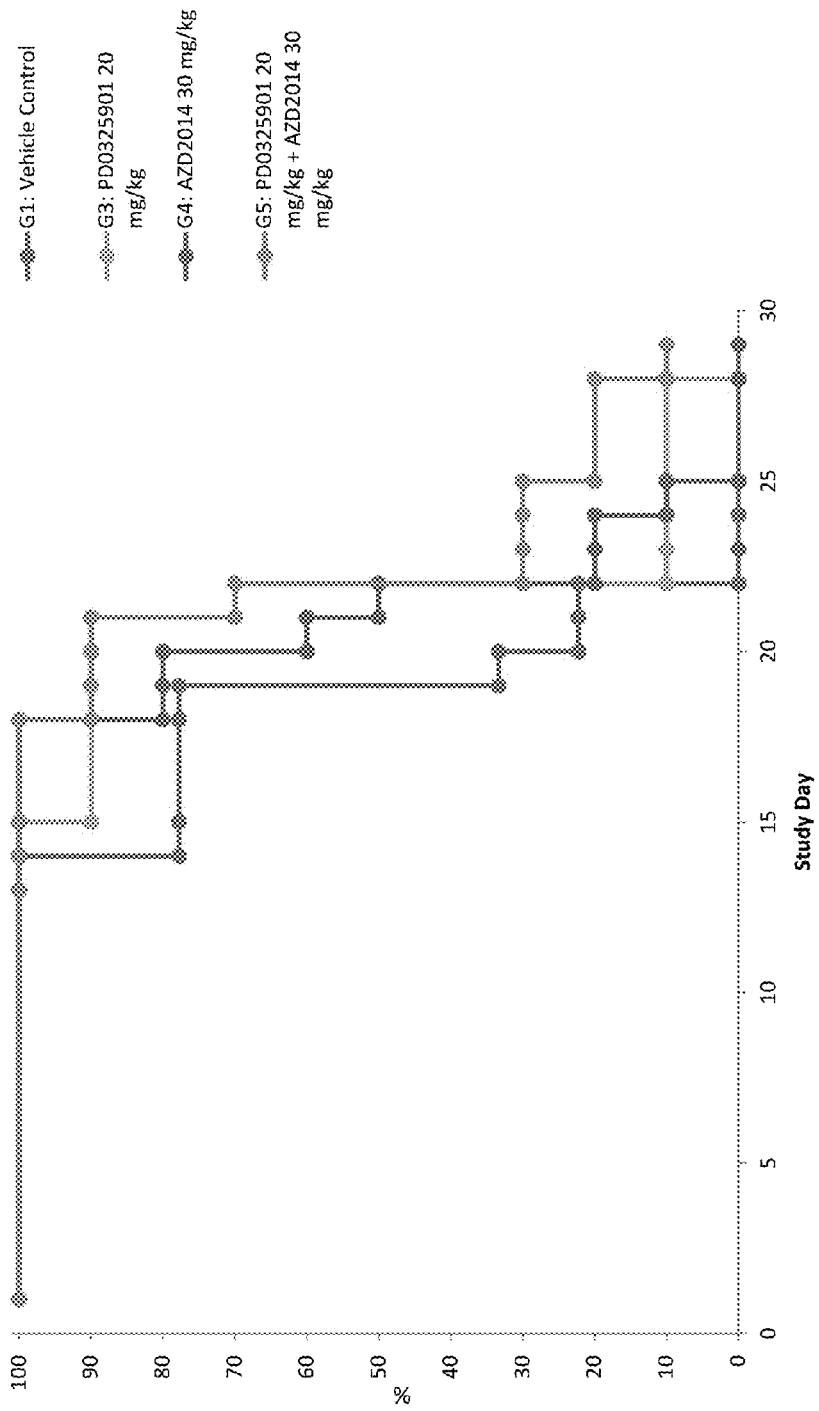
FIG. 18 is a graph representing the impact of various treatments on the survival of mice with patient-derived xenografts from a metastatic tumor.

Next, referring to FIG. 16, data from molecular analyses of the patient of FIG. 15A-15C revealed that targeting of mTOR and MEK could provide positive results for the patient. The data in FIG. 16, illustrates that the combination of the named rapalogs (ridaforolimus, everolimus, temsirolimus, and AZD8055) and the MEK inhibitor PD0325901 provides reduced viability for the patient's tumor-derived cells. Moreover, as illustrated in FIGS. 17 and 18, the combination of the MEK inhibitor (PD0325901) and the mTOR inhibitor (AZD2014) provide the best therapeutic result (FIG. 17) and improved survival of mice with patient-derived xenografts (FIG. 18).

Overall, the instant preclinical model systems and methods provide advances in the area of therapeutics and diagnostics for metastatic cancer. In the instant application, the applicant has reported on characterized patient-derived xenografts of metastatic tumors that are histologically and molecularly characteristic of their original patient tumors, which provides researchers and clinicians with the most molecularly characterized and most comprehensive approached to patient-derived xenografts. This approach is useful for preliminary preclinical studies by making genomics-based rational drug selections.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A method of developing a preclinical model of a metastatic cancer, the method comprising the steps of:
obtaining a sample of a primary tumor from a subject;
obtaining a sample of a metastatic tumor from the subject;
isolating nucleic acids from a first portion of the sample of the primary tumor and a first portion the sample of the metastatic tumor;
determining an allelic status of several markers in the sample of the primary tumor and the sample of the metastatic tumor by performing at least one of whole-exome sequencing, whole-genome sequencing, and whole-transcriptome sequencing on the nucleic acids isolated from the sample of the primary tumor and the sample of the metastatic tumor wherein determining the allelic status comprises identifying a genetic alteration in the several markers;
introducing a second portion of the sample of the metastatic tumor into a model organism to create a subject-derived xenograft;
creating an in vitro cell line using a third portion of the sample of the primary tumor or a third portion the sample of the metastatic tumor;
confirming the allelic status of the several markers in the sample of the primary tumor or the metastatic tumor by isolating nucleic acids from the subject-derived xenograft and the in vitro cell line and performing at least one of whole-exome sequencing, whole-genome sequencing, and whole-transcriptome sequencing on the nucleic acids isolated from the subject-derived xenograft and the in vitro cell line to identify overlapping genomic information corresponding to the allelic status of the several markers provided by the primary tumor or the metastatic tumor and by the subject-derived xenograft and in vitro cell line; and
further comprising administering combination drugs to the model organism comprising the subject-derived xenograft;
wherein the combination drugs are selected based on the allelic status of the several markers in the sample of the primary tumor or the metastatic tumor confirmed in the subject-derived xenograft and the in vitro cell line and based on efficacy of the combination drugs in controlling tumor growth in the subject-derived xenograft; and
wherein the several markers are alterations in genes encoding ERBB2 and PI3 kinase enzymes and the combination drugs comprise BKM120 and/or dacomitinib.

2. The method of claim 1 and further comprising DNA methylation analysis prior to determining the allelic status of the several markers.

3. The method of claim 1, wherein the whole-genome sequencing comprises long insert whole genome sequencing.

4. The method of claim 1, wherein the model organism is a NOD scid gamma mouse.

5. The method of claim 1, wherein the sample of the metastatic tumor is orthotopically administered to the model organism.

6. The method of claim 1, wherein the sample of the metastatic tumor is administered in a flank of the model organism.

7. The method of claim 1 wherein the allelic status comprises single nucleotide variations, insertions/deletions, inversions, translocations, heterochromatic insertions, differentially methylated sequences relative to a reference gene, and/or copy number variations in the several markers.

8. The method of claim 1, wherein the metastatic tumor is found in the central nervous system of the subject.

9. The method of claim 1, wherein the primary tumor is resected from a region of the subject selected from the group consisting of a breast and a lung.

10. The method of claim 1, wherein the overlapping genomic information is an overlap in copy number variation.

11. A method of developing a preclinical model of a metastatic cancer, the method comprising the steps of:
obtaining a sample of a primary tumor from a subject;
obtaining a sample of a metastatic tumor from the subject;
isolating nucleic acids from a first portion of the sample of the primary tumor and a first portion the sample of the metastatic tumor;
determining an allelic status of several markers in the sample of the primary tumor and the sample of the metastatic tumor by performing at least one of whole-exome sequencing, whole-genome sequencing, and whole-transcriptome sequencing on the nucleic acids isolated from the sample of the primary tumor and the sample of the metastatic tumor wherein determining the allelic status comprises identifying a genetic alteration in the several markers;
introducing a second portion of the sample of the metastatic tumor into a model organism to create a subject-derived xenograft;
creating an in vitro cell line using a third portion of the sample of the primary tumor or a third portion the sample of the metastatic tumor;
confirming the allelic status of the several markers in the sample of the primary tumor or the metastatic tumor by isolating nucleic acids from the subject-derived xenograft and the in vitro cell line and performing at least one of whole-exome sequencing, whole-genome sequencing, and whole-transcriptome sequencing on the nucleic acids isolated from the subject-derived xenograft and the in vitro cell line to identify overlapping genomic information corresponding to the allelic status of the several markers provided by the primary tumor or the metastatic tumor and by the subject-derived xenograft and in vitro cell line; and
further comprising administering combination drugs to the model organism comprising the subject-derived xenograft;
wherein the combination drugs are selected based on the allelic status of the several markers in the sample of the primary tumor or the metastatic tumor confirmed in the subject-derived xenograft and the in vitro cell line and based on efficacy of the combination drugs in controlling tumor growth in the subject-derived xenograft; and
wherein the several markers are alterations in genes encoding MEK mitogen-activated kinase (MEK) and mTOR kinase enzymes and the combination drugs comprise AZD2014 and/or PD0325901.

12. The method of claim 11, further comprising DNA methylation analysis prior to determining the allelic status of the several markers.

13. The method of claim 11, wherein the whole-genome sequencing comprises long insert whole genome sequencing.

14. The method of claim 11, wherein the model organism is a NOD scid gamma mouse.

15. The method of claim 11, wherein the sample of the metastatic tumor is orthotopically administered to the model organism.

16. The method of claim 11, wherein the sample of the metastatic tumor is administered in a flank of the model organism.

17. The method of claim 11, wherein the allelic status comprises single nucleotide variations, insertions/deletions, inversions, translocations, heterochromatic insertions, differentially methylated sequences relative to a reference gene, and/or copy number variations in the several markers.

18. The method of claim 11, wherein the metastatic tumor is found in the central nervous system of the subject.

19. The method of claim 11, wherein the primary tumor is resected from a region of the subject selected from the group consisting of a breast and a lung.

20. The method of claim 11, wherein the overlapping genomic information is an overlap in copy number variation.

\* \* \* \* \*